(12) United States Patent
Kennedy et al.

(10) Patent No.: US 10,311,207 B2
(45) Date of Patent: *Jun. 4, 2019

(54) HEALTHCARE SYSTEM AND METHOD FOR RIGHT-TIME CLAIMS ADJUDICATION AND PAYMENT

(71) Applicant: First Data Corporation, Greenwood Village, CO (US)

(72) Inventors: Beverly Kennedy, Greenwood Village, CO (US); Robyn Bartlett, Omaha, NE (US)

(73) Assignee: First Data Corporation, Greenwood Village, CO (US)

( * ) Notice: Subject to any disclaimer, the term of this patent is extended or adjusted under 35 U.S.C. 154(b) by 944 days.

This patent is subject to a terminal disclaimer.

(21) Appl. No.: 14/310,978

(22) Filed: Jun. 20, 2014

(65) Prior Publication Data

US 2014/0372143 A1 Dec. 18, 2014

Related U.S. Application Data

(63) Continuation of application No. 11/428,219, filed on Jun. 30, 2006, now Pat. No. 8,788,293.

(Continued)

(51) Int. Cl.
*G06F 19/00* (2018.01)
*G06Q 10/00* (2012.01)
(Continued)

(52) U.S. Cl.
CPC ........... *G06F 19/328* (2013.01); *G06Q 10/00* (2013.01); *G06Q 10/10* (2013.01); *G06Q 20/20* (2013.01);
(Continued)

(58) Field of Classification Search
CPC ..................................................... G06Q 40/08
See application file for complete search history.

(56) References Cited

U.S. PATENT DOCUMENTS 6,032,859 A    3/2000  Muehlberger et al.
6,208,973 B1 *  3/2001  Boyer .................... G06Q 20/02
                                                                          705/2

(Continued)

OTHER PUBLICATIONS

The American Heritage College Dictionary, Third Edition, Houghton Mifflin Co., New York, 1997, 1993, pp. 817-818 and p. 956, 5 pages total.
Newton's Telecom Dictionary, CMP Books, San Francisco, CA, 2004, p. 687, 3 pages total.

*Primary Examiner* — Joseph D Burgess
(74) *Attorney, Agent, or Firm* — Kilpatrick Townsend & Stockton LLP

(57) ABSTRACT

A system and method for permitting real-time payment of healthcare charges from multiple sources of payment. A POS terminal is used to enter a patient ID and treatment code. A health insurance network receives the patient ID and treatment code and returns an estimated explanation of benefits (EOB) data packet that is used to display an EOB statement at the POS terminal, the display including information on a patient portion not covered by the health insurance plan. The EOB data packet is used to electronically process payment for the patient portion from a second payment source, such as an medical savings account (MSA), credit card account or banking account.

23 Claims, 15 Drawing Sheets

Related U.S. Application Data

(60) Provisional application No. 60/696,269, filed on Jul. 1, 2005.

(51) Int. Cl.
  *G06Q 40/08*  (2012.01)
  *G06Q 50/24*  (2012.01)
  *G06Q 10/10*  (2012.01)
  *G06Q 20/20*  (2012.01)
  *G06Q 30/04*  (2012.01)
  *G06Q 50/22*  (2018.01)

(52) U.S. Cl.
  CPC ............ *G06Q 30/04* (2013.01); *G06Q 40/08* (2013.01); *G06Q 50/24* (2013.01); *G06Q 50/22* (2013.01)

(56) References Cited

U.S. PATENT DOCUMENTS

| | | |
|---|---|---|
| 7,072,842 B2 | 7/2006 | Provost et al. |
| 7,263,493 B1 | 8/2007 | Provost et al. |
| 7,346,523 B1 | 3/2008 | Provost et al. |
| 7,438,218 B2 | 10/2008 | Dooley et al. |
| 7,962,350 B1 | 6/2011 | Provost et al. |
| 8,788,293 B2 | 7/2014 | Kennedy et al. |
| 2001/0027403 A1 | 10/2001 | Peterson et al. |
| 2003/0009355 A1 | 1/2003 | Gupta |
| 2003/0069760 A1 | 4/2003 | Gelber |
| 2003/0200118 A1* | 10/2003 | Lee ................ G06Q 20/04 705/2 |
| 2005/0033604 A1 | 2/2005 | Hogan |
| 2005/0060184 A1 | 3/2005 | Wahlbin |
| 2008/0033750 A1 | 2/2008 | Burriss et al. |

* cited by examiner

| PATIENT ACCOUNT |
|---|
| PATIENT ID |
| PATIENT INSURANCE ID |
| PATIENT MSA ID |
| OTHER PATIENT FINANCIAL ACCOUNTS |
| OTHER PATIENT DATA |

FIG. 4

ABC Insurance Co.

Explanation of Benefits Statement

Insured Name: Joe Insured
Insured ID/SS#: 123-45-6789
Policy: 24680246    Cert:
Claim Number: AB-13579135-001-2-03-40-0005
Control Number: 987654321
Date: 04/05/2006

Patient Name: Pat I Insured
Provider Name: Phyllis A Provider, MD
Patient ID/SS#: 246-80-2468
Patient Account#: YZ1357924680

602  604  606  608  610  612  616

| Service Code | Service Description | Service Date(s) | Provider Charge | Allowed Amount | Discount Amount | Not Covered | Deductible | Copay | Pay At | Remarks | Amount Paid |
|---|---|---|---|---|---|---|---|---|---|---|---|
| 1234 | Physician | 01/27/2006 | $184.00 | $139.00 | $45.00 | | $139.00 | | | 0054 | $0.00 |
| 5678 | Lab Expense | 01/27/2006 | $18.00 | $9.37 | $8.63 | | $9.37 | | | 0054 | $0.00 |
| 1357 | Lab Expense | 01/27/2006 | $13.00 | $4.93 | $8.07 | | $4.93 | | | 0054 | $0.00 |
| 9024 | Lab Expense | 01/27/2006 | $10.00 | $4.44 | $5.56 | | $4.44 | | | 0054 | $0.00 |
| TOTALS | | | $225.00 | $157.74 | $67.26 | | $157.74 | | | | $0.00 |

Remarks
0054    Network Benefits applied. Your provider has agreed to the negotiated rate in accordance with the Managed Care provider agreement. You should not be billed for this amount.

622

| Plan Accumulations – Deductible and Out-Of-Pocket | | |
|---|---|---|
| This Year | 2006 | |
| | YTD | Remaining |
| Family Deductible | $157.74 | $4,842.26 |

| MSA Account | |
|---|---|
| This Year Contributions | $2,000.00 |
| This Year Available | $1,953.50 |

630

| Patient Portion | |
|---|---|
| Submit to MSA        Y/N | |
| Pay To    Provider    ☐ | |
|                 Patient    ☐ | |

632

| Any Remaining Balance |
|---|
| ☐ Pay From Credit Card No ########### |
| ☐ Pay From Other Credit Card _____ |
| ☐ Pay From Checking Account No. ###### |
| ☐ Pay From Other Account No. ######## |

| Payment Summary | |
|---|---|
| Payment Sent To: | Physician Affiliate |
| Payment Amount: | $0.00 |
| Payment Date: | 04/05/2006 |
| Patient's Portion: | $157.74 |

| Total Payment Summary | |
|---|---|
| Payment(s) Sent To: | |
| Payment Amount: | $0.00 |
| Payment Date: | 04/05/2006 |
| *TOTAL PATIENT PORTION: | $157.74 |

620

*remit patient portion directly to provider

Print and Retain This Statement for Patient

FIG. 7

ESTIMATE OF CHARGES

INSURER: ABC INSURANCE CO.

| | |
|---|---|
| Insured Name: | Joe Insured |
| Insured ID/SS#: | 123-45-6789 |
| Policy: | 24680246    Cert: |
| Claim Number: | AB-13579135-001-2-03-40-0005 |
| Control Number: | 987654321 |
| Date: | 04/05/2006 |

THIS IS A PRELIMINARY ESTIMATE OF CHARGES FOR TODAY'S SERVICE. A CLAIM HAS BEEN ELECTRONICALLY SUBMITTED TO YOUR INSURER. PATIENT PORTION WILL BE DEBITED FROM YOUR ACCOUNT. ANY OVERPAYMENT WILL BE CREDITED TO THAT SAME ACCOUNT.

| | | | | |
|---|---|---|---|---|
| Patient Name: | Pat I Insured | | Patient ID/SS#: | 246-80-2468 |
| Provider Name: | Phyllis A Provider, MD | | Patient Account#: | YZ1357924680 |

1402  1404  1406  1408  1410  1412  1413  1418

| SERVICE CODE | SERVICE DESCRIPTION | SERVICE DATE(S) | PROVIDER CHARGE | ALLOWED AMOUNT | DISCOUNT AMOUNT | AMOUNT NOT COVERED | COPAY |
|---|---|---|---|---|---|---|---|
| 1234 | Physician | 01/27/2006 | $184.00 | UNKNOWN | N/A | | $20.00 |
| 5678 | Lab Expense | 01/27/2006 | $18.00 | UNKNOWN | N/A | | |
| 1357 | Lab Expense | 01/27/2006 | $13.00 | UNKNOWN | N/A | | |
| 9024 | Lab Expense | 01/27/2006 | $10.00 | UNKNOWN | N/A | $10.00 | |
| TOTALS | | | $225.00 | UNKNOWN | N/A | $10.00 | $20.00 |

| PATIENT PLAN | DEDUCTIBLE: $5,000 | CO-PAYS: 20 OFFICE VISIT | 10 PRESCRIPTION |
|---|---|---|---|
| | NOT COVERED: SERVICE CODES 9000-9999 | | |

Patient Portion

Submit to MSA    Y/N
Pay To    Provider  ☐
          Patient    ☐

1432    1419

Any Remaining Balance

☒ Pay From Credit Card No ###########
☐ Pay From Other Credit Card _____
☐ Pay From Checking Account No. ######
☐ Pay From Other Account No. #########

1420

ESTIMATED PAYMENT PORTION $225.00

YOU HAVE AUTHORIZED PAYMENT FOR $225.00

FIG. 14

HEALTHCARE SYSTEM AND METHOD FOR RIGHT-TIME CLAIMS ADJUDICATION AND PAYMENT

CROSS-REFERENCES TO RELATED APPLICATIONS

This application is a continuation of U.S. patent application Ser. No. 11/428,219, filed Jun. 30, 2006, and entitled "HEALTHCARE SYSTEM AND METHOD FOR RIGHT-TIME CLAIMS ADJUDICATION AND PAYMENT," which is a non-provisional of, and claims benefit to Provisional Patent Application No. 60/696,269, filed Jul. 1, 2005, and entitled "HEALTHCARE SYSTEM AND METHOD FOR RIGHT-TIME CLAIMS ADJUDICATION AND PAYMENT." Each of the above-referenced patent applications is incorporated by reference herein.

BACKGROUND OF THE INVENTION

The present invention relates to systems and methods for paying healthcare charges, particularly where the charges may be allocated among more than one payment source.

Healthcare costs are an issue of significant concern to the government, consumers, health insurance companies and healthcare providers (physicians, hospitals, pharmacies, etc.). Healthcare costs comprise an increasing and disproportionate share of the U.S. economy. There have been many factors identified as leading to these increases in cost. One such factor is the administrative cost in delivering and billing for healthcare services (administrative costs have been estimated to account for as much as 25% or more of the typical healthcare charge). Closely tied to this is a the lack of financial accountability by many providers (due to the typical patient not being aware of or responsible for the overall cost of received healthcare services). For example, a relatively "routine" hospital stay can easily exceed $10,000, and even with a deductible paid by the patient (say, $500), very little of the total cost is paid by the patient. There is little incentive for the patient to review and question the accuracy of the invoice for services performed at the hospital (when, in fact, the patient may be in the best position to know whether individual services charged were provided or even requested).

Changes are occurring in the healthcare system in order to control costs. One such change has been the increasing use of "consumer-driven" healthcare insurance policies or plans. These plans often feature a high annual deductible (e.g., $5,000), coupled with a medical savings account (MSA). The consumer contributes to the MSA (usually pre-tax) and may be able to accumulate significant funds over time in which to pay for medical costs not covered by the high deductible insurance policy. The payment of charges from an account "owned" by the consumer is believed by many to lead to more careful decisions by consumers who may be requesting and monitoring the cost of medical services.

Consumer-driven programs may result in financial/accounting difficulties for some providers. It may be difficult for the consumer and for the provider (particularly a physician at a small medical office without sophisticated billing or transaction processing systems), to keep track of an annual deductible and how an individual charge may be allocated between an insurance company (or other third party payer) and a consumer. At the time of rendering the service, a provider often will have no data available for indicating whether or not a deductible has been met (prior charges applied to the deductible may have been billed by other providers), and such data can be obtained only by submitting a claim to the consumer's insurance company. Further, an important feature of most healthcare policies is that the consumer is able to take advantage of a schedule of "authorized" or "permitted" charges for specific services (usually identified by treatment codes) that are governed by an agreement negotiated between the provider and the insurer. Such permitted charges are usually far less than the full, undiscounted charge to be paid by someone without insurance. The provider has agreed with the insurer to receive no more than the permitted charge for services provided to covered consumers. Thus, even if the deductible has not been met (which will usually be the case for a person without large annual medical bills), the amount to be paid by the consumer will not be the physician's "normal" charge, but rather the insurer's "permitted" charge. Unfortunately, many providers have contracts with multiple insurance companies, health maintenance organizations (HMOs), or other healthcare payers, and the discounts (and ultimate charges to be paid) for the same services are not the same, but rather will vary from patient to patient (depending on the insurance program that covers the patient). Many providers are unable to confirm the permitted charge until after a claim is submitted and adjudicated by the insurance company.

It can therefore be long after a healthcare service is provided that a charge becomes payable by the consumer. The provider will first submit a claim to the consumer's insurer, and wait for a claim adjudication—usually in the form of an "Explanation of Benefits" (EOB) statement to the consumer from the insurer (a similar statement usually sent at the same time to the provider is often referred to as an "Explanation of Payment" or "EOP"). The EOB will show the permitted charge for the services, and in those cases where the deductible has not been met, confirm that the permitted charge is the patient's responsibility. While the EOB will provide confirmation of what is to be paid by the consumer, it will often take weeks (sometimes months) for the EOB to issue and for the provider to thereafter bill for the permitted charge and to then receive payment from the consumer. In cases where a provider has many patients with "high deductible" plans, a provider may have substantial outstanding charges that are awaiting a determination of the permitted amount and a determination of the paying party (insurance company or consumer). For an individual provider, the delay in receiving such payments can be a significant financial burden.

BRIEF SUMMARY OF THE INVENTION

There is provided, in accordance with embodiments of the present invention, a network/system and method for providing claim adjudication and payment for a healthcare charge.

In one embodiment, a system provides right-time payment for patient healthcare services to a provider of such services. The system includes a point of sale (POS) device for use by the provider in entering patient information, including at least patient ID information and a healthcare treatment code, and a host for receiving the patient information from the POS device for submission as a healthcare claim to a first payer source. The host also provides estimated explanation of benefits (EOB) information. The estimated EOB information includes at least information on any patient portion of a provider charge that is not to be paid by the first payer source, so that the patient may pay the patient portion on a real-time basis to the provider in response to the estimated EOB information.

In another embodiment, the first payer subsequently returns actual (non-estimated) EOB information, and such actual EOB information is reconciled against the earlier estimated EOB information.

In some embodiments, claim adjudication may be achieved by estimating amounts to be paid (e.g., to be paid by a third party payer or by the patient), in response to a healthcare claim. In other embodiments, some payers provide real-time claim adjudication and some do not. The system may receive real-time, actual EOB information relating to some payers (real-time adjudication of a claim) and estimated EOB information relating to other payers (e.g., an estimating system estimates EOB information, but actual adjudication and actual EOB information may be provided later). In either instance, payment can be made by the patient based on information provided at the time a healthcare claim is made. This type of transaction, where payment may be made by a patient immediately (based on either estimated or actual EOB information), is sometimes referred to herein as "right-time" claim adjudication.

A more complete understanding of the present invention may be derived by referring to the detailed description of the invention and to the claims, when considered in connection with the Figures.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

FIG. 4 illustrates a patient account set up at the provider host.

FIG. 7 is screen display at the POS terminal of a healthcare provider, illustrating data sent as part of the EOB data packet.

FIG. 14 is a screen display at the POS terminal of a healthcare provider, illustrating data sent as an estimated EOB in accordance with another embodiment of the invention.

DETAILED DESCRIPTION OF THE INVENTION

Figure 1:
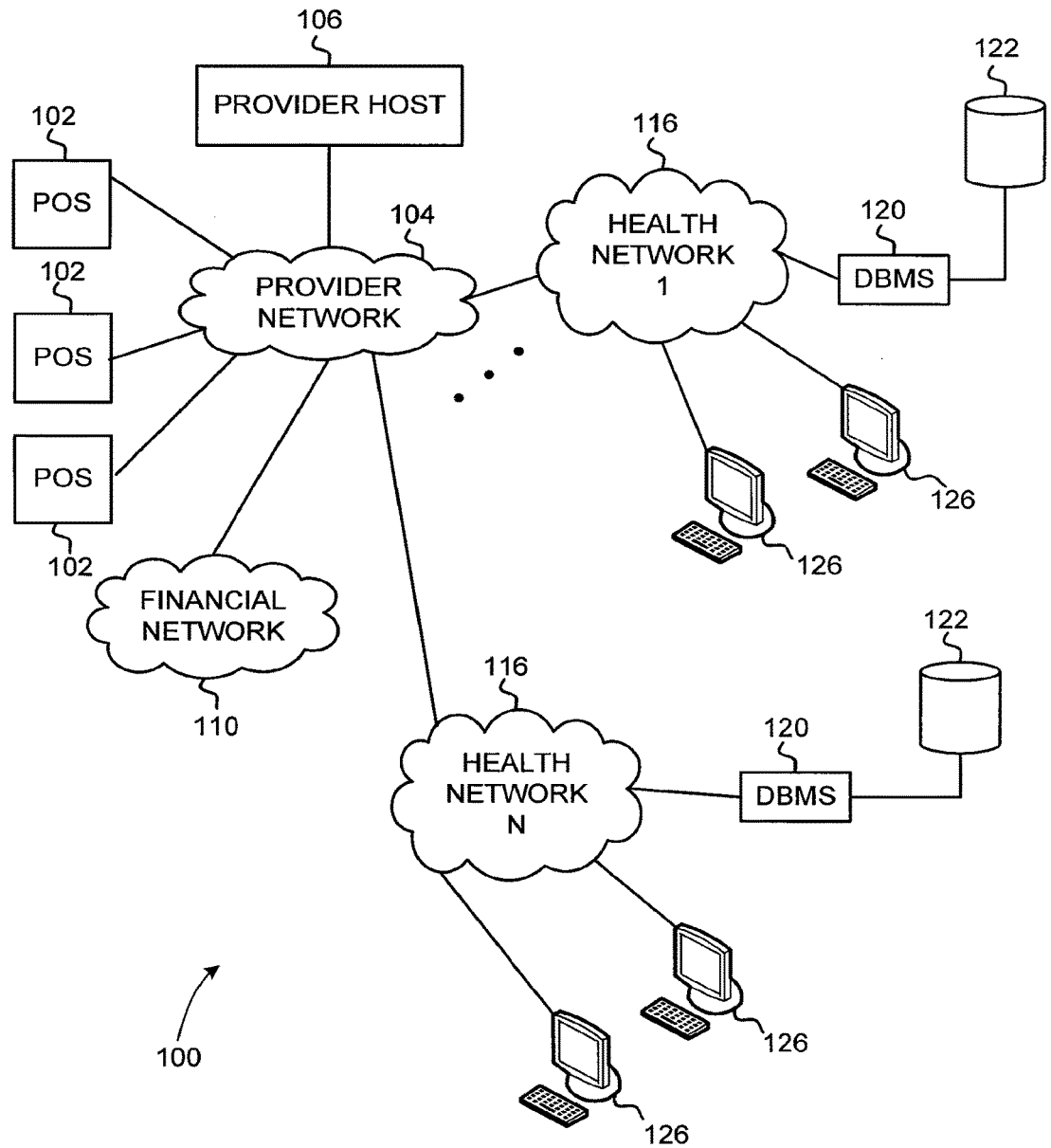
FIG. 1 is a general block diagram showing a system for providing real-time claim adjudication and payment in accordance with one embodiment of the invention.

There are various embodiments and configurations for implementing the present invention. Generally, various embodiments of the present invention provide systems and methods for permitting a healthcare provider to obtain real-time or right-time claim adjudication of a healthcare claim, and to obtain real-time payment processing of the patient's portion of a healthcare charge at the time services are provide to the patient or consumer.

Some embodiments of the invention use a POS ("point of sale" or "point of service") terminal in order for a healthcare provider to have real-time access to healthcare payment information used by a payer for adjudicating claims. The term "provider" is intended to encompass any person or entity that provides a health-related service to a patient or consumer, including a physician (or other healthcare professional), clinic, hospital, treatment center, medical testing laboratory, pharmacy, dispensary, health-related store, and the like. While the term "service" is used herein, it should be understood that such term is meant to include not only medical and other health-related services, but also physical products and supplies, such as pharmaceuticals, over the counter drugs, devices, equipment and other healthcare products that may be provided during treatment or otherwise purchased by the consumer for health or medical purposes.

Embodiments of the invention permit a healthcare provider to obtain real-time claim submission, adjudication, and payment processing (and in some cases, estimated adjudication but real-time payment processing), such as (but not limited to) when the patient has a high deductible healthcare policy or program, and where the patient portion of the charge is determined only after the claim has been processed or adjudicated. The term "payer" may be a third party payer, such as a health insurance company, health maintenance organization (HMO), third party administrator, self-insured employer, and the like. Such a payer is sometimes referred to as a first or "principal" payer, since claims are first made to that entity and any portion not covered are then the responsibility of the patient. However, the patient may have a secondary payer or payment source, such as an MSA account, credit card account, or perhaps the patient's own funds (from cash, checking account, etc.). Various embodiments of the invention permit the provider (and patient) to learn the amount covered or not covered by the insurer or third party payer at the time the service is provided (for example, by the use of an estimating system), so that the provider can request payment at that time for any amount owed by the patient (and not to be paid by the insurer or third party payer).

It is to be understood that while the terms "medical savings account" and "MSA" are used herein, those terms are for convenience in referring to accounts set up (usually with pre-tax dollars) to pay medical costs, often under tax code and other governmental regulations. The terms are intended to encompass all accounts set up for similar purposes, such as those also known as health saving accounts (HSAs), flexible spending accounts (FSAs) and health reimbursement accounts (HRAs), and the like. Also, payments of a patent's portion of a charge may be made from many different kinds of financial accounts (other than MSAs), such as line-of-credit accounts, checking accounts, branded credit and debit card accounts (VISA®, MasterCard®, American Express®, Discover®, etc.) and private label or branded accounts (maintained by pharmacies, health networks, and the like).

Some systems are implemented by the provider entering information at the POS terminal regarding the patient and a treatment. Such information is used to generate an electronic claim that is submitted to the third party payer, with EOB data generated and returned in real-time fashion by the insurer (or an estimating system) for display at the POS terminal. The EOB data can be used to submit, either automatically or when directed by the patient, a request for reimbursement or payment from an MSA account (or other payment source) for the patient portion of the charge, without the patient having to separately submit such claim. The EOB data is used in its electronic form for such purpose, and since it represents in some instances the results of a processed insurance claim, it is suitable for confirming the amounts which are permitted to be charged by the provider as well validly document the basis for an MSA payment request on behalf of a consumer. In other instances, where estimated (preliminary) EOB information is returned, the patient will have a basis for understanding the likely amount to be processed for MSA payment when the final adjudication is made.

It should be understood that the term "EOB" (explanation of benefits) is used herein in its broadest sense, to refer to any form of data resulting from a processed healthcare claim or inquiry. Thus, the term "EOB" also includes EOP (explanation of payment) statements that are sent to a provider, as well as other forms of electronic remittance advice records or documents defined under various industry standards, such as ANSI 835, and other data messages, such as data messages having estimated patient or health network payment information (e.g., prepared by a third party processor).

In one embodiment, transactions are handled in a real-time, on-line basis through the use of a patient card (issued, e.g., by the patient's insurer) which electronically identifies the patient. The card may be used to access an account maintained by the provider, which account includes not only medical records of the patient but also financial data such as MSA account identification and information on other accounts that might be used by the patient to make payment on a bill (credit card, checking, other banking accounts, etc.). In this way, once the EOB data is returned by an insurer in response a medical claim, the provider host (or other host) can access other account information of the patient to provide for final settlement of the bill for services, particularly any amount not to be paid by the principal payer or insurer.

Turning now to FIG. 1, a system 100 includes a plurality of POS terminals 102. The terminals 102 communicate through a provider network 104 to a provider host 106. In one embodiment, the network 104 is operated by the provider in a single office and used by both healthcare professionals (e.g., to retrieve patient medical records) and by administrative and billing staff (to submit claims and arrange for payment). In other embodiments, the network 104 may be used by individual providers that are geographically dispersed but rely on the network 104 to implement a single source of automated claims processing at the provider host 106. While the POS terminals 102, network 104 and host 106 may perform a variety of processing, retrieval and display functions, the description herein will be directed to those functions as they relate to healthcare claims processing and payment.

In order to process a claim for payment (based on services rendered by the provider), at least one of the terminals 102 is capable of entering data to identify the patient and to enter treatment codes required to identify the services rendered. The terminal 102 may be a terminal of the type described in U.S. patent application Ser. No. 11/153,218, filed Jun. 14, 2005, entitled "Healthcare Eligibility Verification and Settlement Systems and Methods, which terminal has an integrated display, card reader and keyboard to facilitate electronic entry of a patient ID from a card presented by the patient, as well as entry of treatment codes and other data at the keyboard. Such application is hereby incorporated by reference. Alternatively, the POS terminal 102 may be a personal computer having a connected display screen, card reader, keyboard (e.g., for entering data manually if a patient does not have a machine readable card or the card is not present), or other devices for entering and displaying data, and programmed to perform the functions described herein. For example, the personal computer may have an internet browser program to facilitate entering, displaying and using data in accordance with a web application resident at the provider host 106 or resident at a host within a third party network or system (not shown in FIG. 1). Furthermore, the terminal 102 may be integrated with a provider's desktop management practice system—applications providing scheduling, electronic patient records, clinical information, patient billing, and so forth—so that data from real time claim processing (to be described in greater detail later) can be incorporated and used as necessary in those applications (e.g., updating accounts receivables). Alternatively, those applications may reside at the provider host 106.

Also, the terminal 102 could include or be associated with biometrics-based systems for identifying the patient (e.g., using handwriting, retinal scans, finger prints, and so forth).

The provider host 106 may maintain data (such as financial and insurance information) for each patient, and mange the flow of data between the terminals 102, and through the network 104 to a banking or financial network 110 and to one or more external health networks 116. The financial network 110 is for handling conventional credit card, debit card and similar financial transactions. Each health network 116 may be operated by a different third party payer (insurer, HMO, etc.) and links systems, terminals and databases operated by the third party payer. In many cases, the third party payer will have an agreement with a provider to treat consumers covered by that third party's plan at specified or "permitted" charges. The health networks 116 each have an associated database management system (DBMS) 120, which manages a database 122, and terminals 126. The database 122 stores data such as claims history, pending claims, permitted charges (e.g., flat fees or a discount off the provider's normal charges), deductibles, co-pays and other information used for processing claims and generating electronic EOBs (to be describe in greater detail later). The DBMS 120 and database 122 may include any one of numerous forms of storage devices and storage media, such as solid state memory (RAM, ROM, PROM, and the like), magnetic memory, such as disc drives, tape storage, and the like, and/or optical memory, such as DVD. The database 122 may be co-located with the DBMS 120, it may be integral with the DBMS 120, or it may represent (with DBMS 120) distributed data systems located remotely in various different systems and locations. The terminals 126 are workstations used, for example, by administrative staff when accessing the DBMS 120 and other systems connected to the network 116.

The networks 104, 110 and 116 may be implemented using the Internet, an intranet, a wide area network (WAN), a local area network (LAN), a virtual private network, or any combination of the foregoing. The networks may include both wired and wireless connections, including optical links. For example, the POS terminals may include portable wireless terminals (stationary or mobile) linked to the provider network 104 by wireless communications channels. In some cases in a single office, the terminals 102 may include portable wireless terminals to be conveniently carried by an individual provider for use in displaying medical records and entering treatment information, and stationary terminals used by billing or administrative staff to process claims and payments.

Further, while the embodiment of FIG. 1 shows the POS terminals 102, the provider network 104 and the provider host 106 as separate elements, it should be appreciated that in some circumstances all of such elements could be implemented by a single processing system or device with suitable memory (e.g., a programmed personal computer), particularly in a small provider office where only single terminal might be used and where the single terminal or system could be connected via a network (e.g., the Internet) to the financial network 110 and to the one or more health networks 116, or to a third party host/network (not shown) where web applications may be resident.

It should be appreciated that the relationship between payers and the health networks 116 and the financial network 110 can be multifaceted and complex. For example, in some instances, the third party payer operating a health network 116 may, in addition to being a principal payer, also be the administrator of an MSA plan for the same patient, and thus an insurance claim submitted to the principal payer may also be processed for an MSA payment at the same time. In other instances, a patient may have multiple principal payers (e.g., where several family members are each insured and there may be overlapping coverage), and thus an insurance claim may need to be submitted to several different health networks 116 (which in turn reconcile claims among themselves). In still other instances, one health network 116 may be a principal payer (for receiving an insurance claim) and another health network 116 or an institution in the financial network may be the patient's MSA administrator. The use of the POS terminals 102 and the provider host 106 for purposes of submitting electronic claims and electronic requests for payments helps reduce delay and overhead to the provider in obtaining real-time payment when there are different or overlapping payers involved.

As mentioned earlier, and as will be described in greater detail later in conjunction with embodiments illustrated in FIGS. 9, 10, 12 and 13, the processing and management of claims (and payment) could take place at a third party host, processor system or network rather than the provider host 106.

Figure 2A:
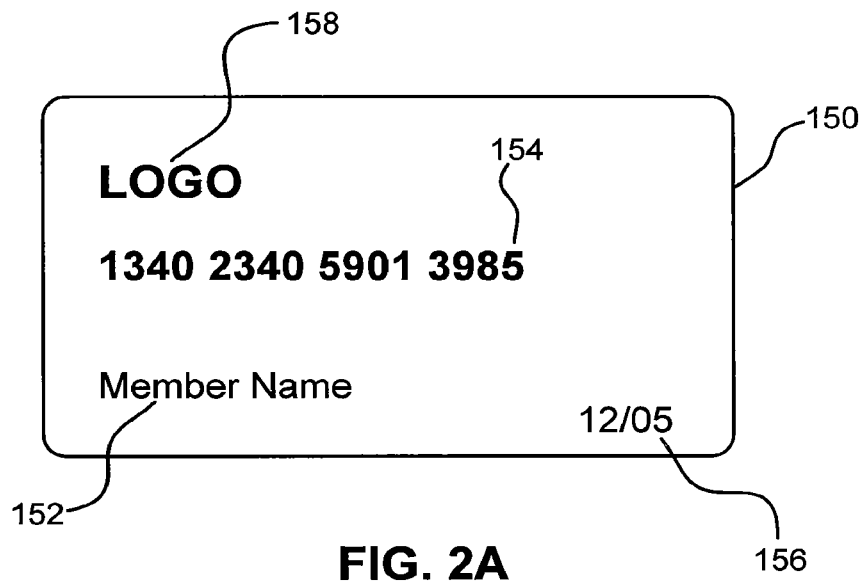
FIGS. 2A and 2B illustrates a healthcare card used in the system of FIG. 1.
Figure 2B:
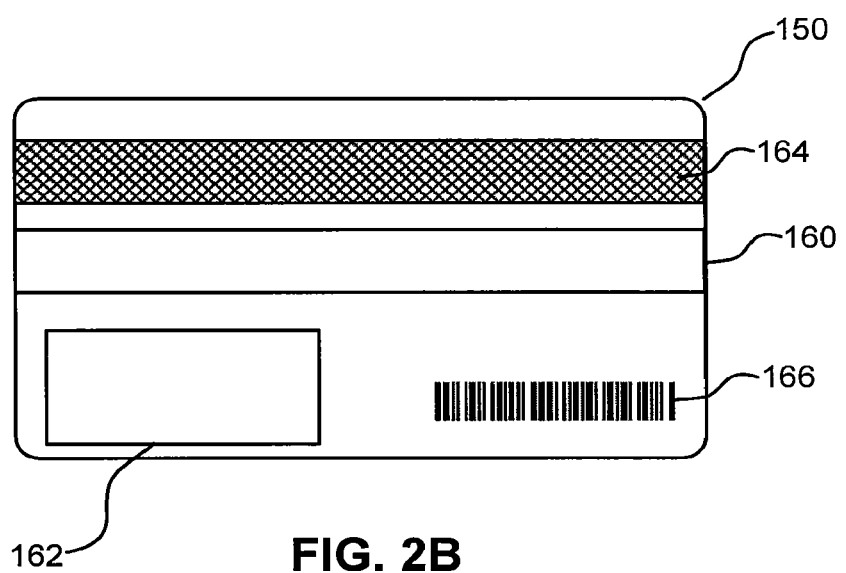

FIGS. 2A and 2B show the front and back sides, respectively, of an identifying presentation instrument or card 150 that could be used by a consumer when visiting a healthcare provider. The card 150 has as its primary purpose the identification of the consumer and the consumer's insurer or third party payer, to assist the provider in processing a claim for reimbursement after services have been provided. However, as should be appreciated, the card may have other purposes as well, such as verifying in advance that the consumer is in fact covered by a healthcare plan before services are provided (i.e., an "eligibility" inquiry). In one embodiment, the card will carry or store electronic data used by the provider to identify a consumer, his/her healthcare plan, and to retrieve other information that may be useful for making payment to the provider.

One side of the card may be embossed with the member's name 152, an account number 154, and an expiration date 156. The card may have a logo 158 of the payer (e.g., insurance company) or the logo of a financial network (VISA®, MasterCard®, American Express®, Discover®, etc.).

The back side of the card may include a signature line 160, and plan information 162. Plan information may include a group number, a plan administrator phone number, and other similar information. For example, while the card is primarily intended to facilitate electronic transactions, it may have useful printed information such as deductibles, co-payments, related account IDs (e.g., MSA account number, credit card information), and the like.

In one embodiment, the card also includes one or more information encoding features. Information encoding features may include a magnetic stripe 164, a bar code 166, a smart chip (not shown), an RFID (radio frequency identity device) and the like. It is to be understood that many other examples of a health care presentation instrument and associated information encoding features are possible.

In the illustrated embodiment, the card number 154 (which can be both physically displayed as well as encoded electronically on the card) identifies the patient and his insurance plan or some other identifier. The card 150 will typically be issued by the insurer, and will have information formatted in accordance with well known industry standards so as to be readable by a card reader (if on a magnetic stripe) or a scanner (if in the form of a bar code). Such information is used by the POS terminal and provider network 104 to access the patient's records, to ultimately process insurance claims and/or route the transaction data to the financial network 110. However, the card 150 need not be issued by the insurer—it could be issued by the provider or a third party (plan administrator, employer, financial institution).

Figure 3:
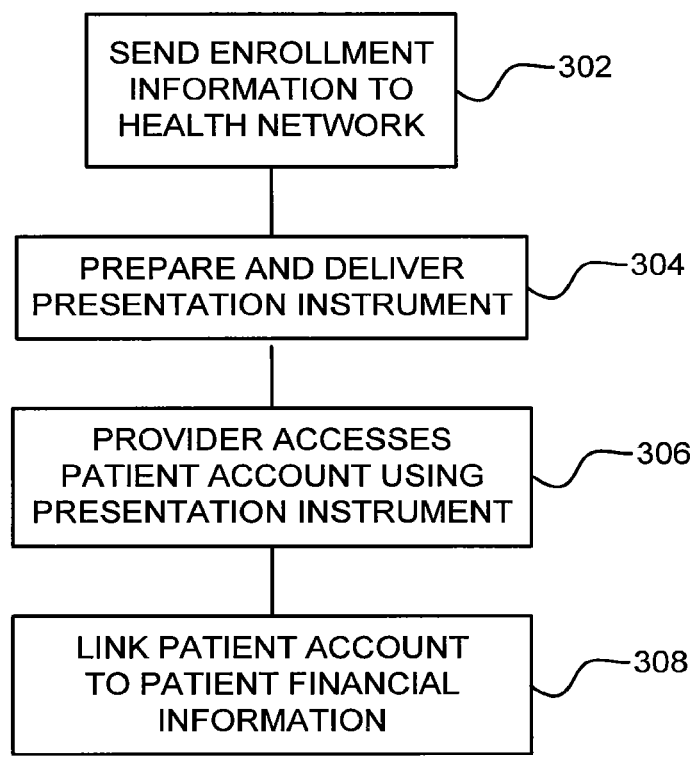
FIG. 3 is a flow diagram illustrating establishment of accounts with patient information in order to permit payment for services provided by a healthcare provider.

FIG. 3 illustrates a process used in one embodiment of the invention for setting up accounts and information that can be used by a provider and patient to seek reimbursement for healthcare claims and make payments for medical services. It should be understood that in the embodiment of FIG. 3, the process involves the creation of two separate data records, one at the health network 116 operated by the insurer of the patient, and the other at the provider network 104 (more specifically at the provider host 106). In FIG. 3, when a patient or consumer first enrolls with a health plan, enrollment information (e.g., identification data, personal information of the consumer and his/her dependents, and health plan information such as details of the coverage, co-pays, deductibles, etc.) is sent to the health plan administrator or insurer and then ultimately stored in a useable form as a data record in the database 122 of the health network 116 (step 302). In some cases, the consumer may send certain kinds of personal information (social security numbers, member IDs, dates of birth, names of primary insured and any dependents, employer name and plan number, etc.) and the insurer will determine the appropriate plan features (deductibles, co-pays, etc.) and load all the needed information into the database 122. In response to the establishment of the health plan account or data record for the patient within the health network 116, a card or presentation instrument (such as the card 150) is issued and sent to the consumer (step 304). After the patient receives the card, and when first presenting the card to a provider, the provider uses the card to access (step 306) the health plan account (e.g., by swiping the card at a card reader). The access initially can be for the purpose of downloading account information from the health plan network in order for the provider to establish its own account for the patient, and storing the account information at the provider host 106.

The account or data record accessed by the provider at step 306 may be used for a number of treatment-related purposes (e.g., to store medical records and information), but in some embodiments of the present invention, the account likewise serves to enable the provider to electronically process claims (and all associated claim message sets and payment transactions. Also, it should be appreciated that in the case of an existing patient, a provider account may already exist, in which case step 306 has as its purpose the linking of the patient's insurance identification data to the existing account.

Finally, in at step 308, the provider will link certain financial information to the account established at step 306. Such linking will include associating the insurance data to other financial accounts that may be used by the patient to settle bills, such as an MSA account, a credit card account, and the like.

It should be appreciated that in some embodiments the insurer itself may collect the financial account and other information useful to the provider when the consumer enrolls in the health plan at step 302. For example, the insurer could collect MSA account information, other financial accounts that might be used to make payment on a "patient portion" of a provider charge, and so forth. This information could be stored at database 122 (for later downloading to the provider host 106), or could be stored electronically on the card 150 and stored directly into the host 106 after the card is read at the terminal 102. Alternatively, the information may be stored or accessed at a third party system (not shown in FIG. 1) that is connected (e.g., via the internet) to both the provider terminals 102 and the health networks 116. In some cases, the patient card could be used to not only identify the patient, but also identify the principal payer and any secondary payer, and such information could be read directly from the card 150 for purposes of preparing claims and requesting payments, without the need for being separately looked up at the host 106. In other embodiments, the card 150 may be used to identify patient and the principal payer or insurer, but the host 106 is then accessed using the patient ID to look-up any secondary payers (e.g., for paying the patient portion of any charge). In other embodiments, the card 150 may be prepared by the provider rather than the insurer (based on information provided by the insurer and the patient), and the card carries encoded data used by the provider when identifying a patient or accessing the patient's record. In yet other embodiments, the card 150 may be a conventional credit or debit card, having sufficient identification data for the patient's account at the host to be accessed, and/or enabling the provider to identify the patient, the patient account or other financial accounts of the patient that may be used to pay provider charges.

FIG. 4 illustrates a patient account that could be set up at the provider host 106. The account for each patient will have several stored components or fields, including the patient ID (this could be one or more IDs assigned to the patient, such as a provider-assigned patient number, patient social security number, or other ID that could be the same as or associated with the patient ID on the card 150), a patient insurance company/plan identifier or ID (this also may have been read from the card 150), a patient MSA identifier or ID (MSA account number, MSA plan/administrator), other patient financial account IDs (these could be patient credit card account numbers, banking or checking account numbers, etc.), and other patient or treatment data (medical or clinical records, medical or payment history), all of which have been entered into the system and associated with the patient. While not seen in FIG. 4, there may also be programs stored at the host that are associated with the patient or his insurance company, such as programs to create a claims form or template that can be electronically submitted to an insurance company or other payer. There may, for course, be different templates or forms associated with each third party payer (insurance company, MSA administrator, Medicare, Medicaid, etc.) to whom the provider may need to submit claims.

Figure 5:
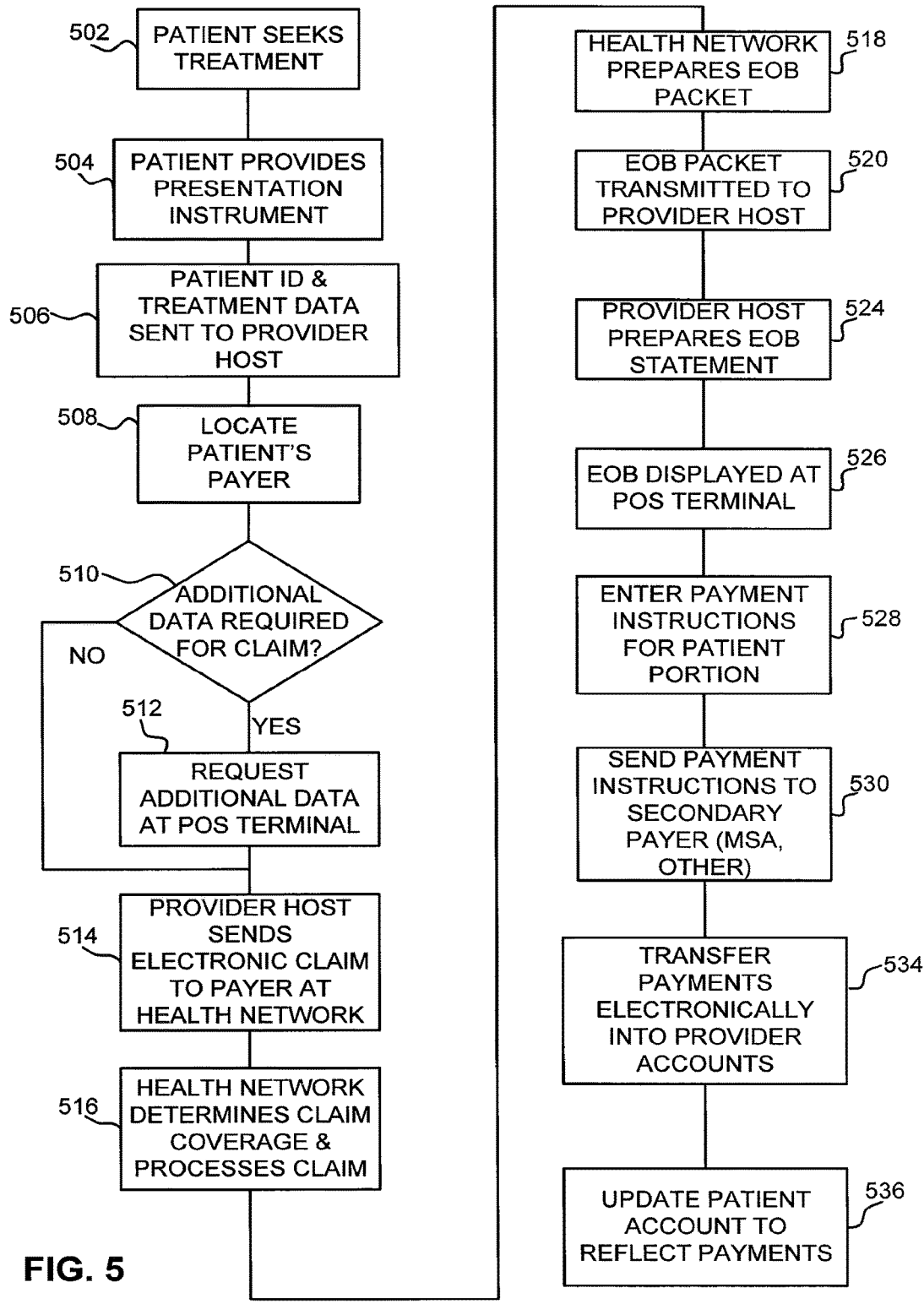
FIG. 5 is a flow diagram illustrating the submission of a real-time claim by a healthcare provider using the system of FIG. 1, resulting in an EOB data packet transmitted to the provider and used to obtain real-time payment for the patient portion of a healthcare charge.

Turning now to FIG. 5, there is illustrated an exemplary process for the submission of an electronic claim by (or on behalf of) a provider, the generation of an electronic EOB, and the use of the EOB to obtain real-time payment from a consumer.

As illustrated, the patient first seeks treatment from a provider at step 502 and then provides the presentation instrument or card 150 at step 504, when the patient's charge is to be processed. The card 150 is read at the POS terminal 102 so the patient's identifying data (along with any treatment data) may be sent to the provider host 106 at step 506. The treatment data may be a code used by the provider and recognized by the third party payer to identify the diagnosis and treatment of the patient, and entered at the POS terminal 102 by the provider. One example of such a code is the CPT® (Current Procedural Terminology) code developed by the American Medical Association.

The provider host performs a look-up of the patient's account information in order to identify or locate the patient's payer (i.e., the insurer or other third party payer) at step 508. In some instances, where specific insurers may require additional information for submitting a claim, the host may request additional data (e.g., the third party payer may require additional information such as a dependent's name, a pre-authorization code, provider ID and the like), steps 510 and 512. Such additional information may be requested at the POS terminal 102 for entry by the provider. Once any additional information is entered, an electronic claim is generated by the host and sent through the network (step 514) to the third party payer (at one of the health networks 116), where at step 516 the claim information is processed by the DBMS 120 (and the patient/insured information is retrieved at the database 122, as required). Among other things, the DBMS will query the database 122 to make sure that the patient is covered/eligible, determine the features of the patients coverage (co-pays, deductibles, etc.), and determine the permitted charge for the treatment rendered by the provider under the claim. The database 122 will also store previous charges that may have been applied to the patient deductible, and the DBMS 120 will determine the extent to which any charge is within the deductible (and to be paid by the patient).

In response to the information submitted with the electronic claim and the query of the database 122, an electronic EOB data packet is created at the health network (step 518)

and sent from the DBMS 120 back to the provider host (step 520), where the EOB information is used to create an EOB statement for display at the POS terminal 102 (steps 524, 526), and where it can be viewed and printed by the provider staff and discussed with (and a printed copy provided to) the patient. It should be pointed out that the electronic EOB displayed, printed and provided to the patient may offer significant administrative advantages and cost savings in the processing and adjudication of healthcare claims. Not only is the submission of the claim by the provider simplified, but the health network uses the provider as its proxy in providing the EOB to the patient, thereby avoiding the cost and expense of preparing and mailing a separate EOB to the patient.

In some embodiments (to be described in detail later), two EOB data packets may be sent to the provider—(1) an estimated EOB and (2) a second, later EOB representing an actual adjudication of the claim by the health plan/payer.

Figure 6:
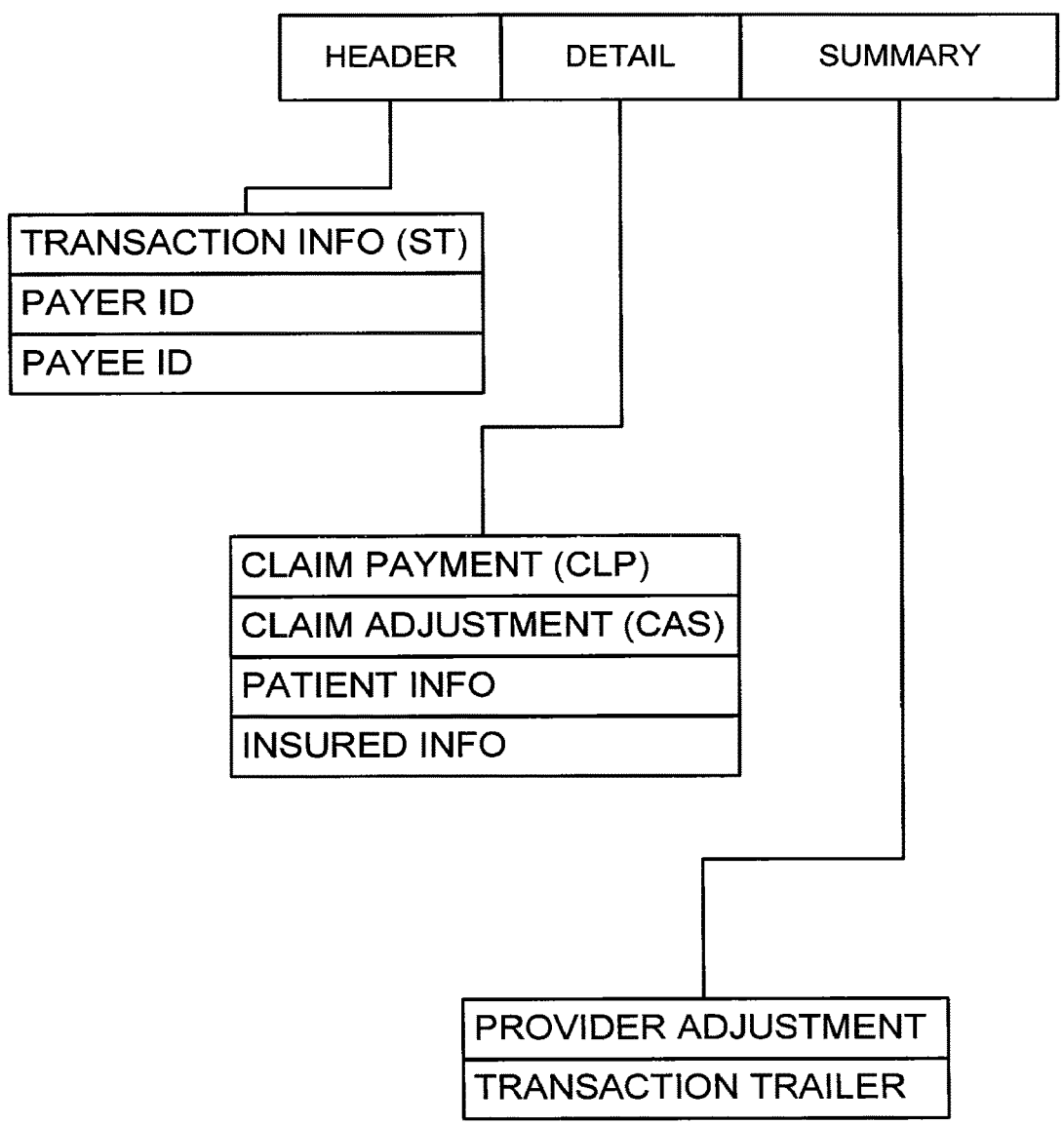
FIG. 6 illustrates the content of a EOB data packet used for creating the display of EOB information and for obtaining payment for the patient's portion of a healthcare charge.

FIG. 6 illustrates the EOB message sent from the DBMS 120 to the provider host 106, for purposes of creating the displayed EOB statement. The message is a data packet— also referred to as an electronic remittance advice (ERA) message—formatted in accordance with ANSI Accredited Standards Committee X12N, "Health Care Claim Payment/Advice 835 Implementation Guide (ASC X12N 835), currently published by Washington Publishing Company (www.wpc-edi.com). As seen in FIG. 6, the data packet or message includes data transmitted in three overall levels (Header, Detail and Summary). The Header level includes Transaction Information (to indicate the start of a transaction), Payer Identification, and Payee Identification. The Detail level includes the data needed for generating and displaying the EOB statement, including Claim Payment (amount of claim submitted, treatment/service codes, etc.), Claim Adjustment (agreed to payment, adjustments to claimed amount, patient responsibility, etc.), Patient Information (patient name and other identification) and Insured Information (insured name and other information). The Summary level includes Provider Adjustment (adjustments not specific to a claim, but due to provider circumstances, such as interest, penalties, capture of previous overpayments, etc.), and finally Transaction Trailer (to indicate the end of the transaction). As mentioned earlier, the EOB or ERA message is used at the provider host 106 to create an EOB statement at the POS terminal 102.

In circumstances where both an estimated EOB and an actual (final) EOB are provided, it is contemplated that both forms of EOB will have the same or similar data levels and fields. However, it should be appreciated that since the estimated EOB is not a final adjudication of the claim, the estimated EOB message may have data less than, different from, or in addition to, the data in the actual EOB message.

FIG. 7 illustrates the display of an EOB statement at the POS terminal 102, using the data contained in the electronic EOB message transmitted from the health network 116. As can be seen, the EOB statement has information pertaining to the claim submitted, including various services (identified by Service Codes 602 and Service Descriptions 604), and for each service or treatment, the Service Date(s) 606, and the Provider Charge 608 submitted by the provider.

As also seen in FIG. 7, the EOB statement includes the Allowed Amount 610 that the payer and provider have agreed to for the particular service (which in the display of FIG. 7 is the Provider Charge 608 less a Discount Amount 612). Certain services may not be covered (e.g., a medical treatment or service that has been expressly excluded under the patient's plan), and as illustrated for each service there is a Deductible 616. In the example shown, the patient has a $5,000 annual deductible, and the Deductible 616 listed in the EOB shows how much of each service is subject to the deductible. Thus in FIG. 7, the total amount of the allowed charges are $157.74 and since the patient has not had previous charges for that year, all of that total amount falls within the deductible and is indicated as a Patient Portion 620.

The EOB statement also displays a Deductible and Out of Pocket Report 622 showing the amount remaining in the patient's deductible after application of the current charges.

Referring to FIG. 7 in conjunction with FIG. 5, in the present example the patient has enrolled in an MSA account and the current available amount for an MSA account is shown below the EOB statement at 630 in the display of FIG. 7. The provider uses the display of FIG. 7 to enter instructions from the patient when any patient portion is to be submitted to an MSA account or other secondary payment source (step 528, FIG. 5), using the payment menu display 632 in FIG. 7. The payment menu 632 includes an entry field for whether a payment should be requested from the MSA account, as well as whether the payment from the MSA should be made to the patient or to the provider (if made to the patient, then the patient will normally be required to make payment at the time of service for any amount to be later reimbursed to the patient out of the MSA account). In some cases, the patient may not have sufficient funds in the MSA account to pay deductibles, and in that case the provider (with patient authorization), may designate at menu 632 that the owed amount is to be paid out of a credit card or other account (such as an account having an account identifier stored at the provider host at step 308).

It should be appreciated that the provider (with the patient's authorization) may at step 530 (FIG. 5) then electronically submit the MSA claim so that the provider may receive payment from the MSA account without the need for awaiting a separately issued EOB statement and then later billing the patient for any deductible or other amounts not covered by the patient's insurance. Also, if the patient does not have an MSA or does not have sufficient funds in the MSA to cover owed amounts, the patient can be asked for a credit card payment or cash as part of the EOB reconciliation process (using the screen of FIG. 7). While not illustrated in FIG. 5, the provider may print the EOB statement for the patient to retain as a record for the transaction.

In addition, the system 100 may expedite an automatic payment to the provider (by the health network), further reducing administrative costs and eliminating delays in settling accounts. Thus, as illustrated in FIG. 5, the financial network 110 may process payments (using a conventional ACH banking network) from the health network 116 to the provider, by electronically processing a bank transaction that debits a health network bank account (for the amount of any insurance payment for the treatment of the patient) and that credits such amount to a bank account of the provider (step 534). Such payment can be reflected at the provider host by updating the patient's individual account and the provider's accounts receivables (step 536). A payment for any patient portion of the charge may also be electronically processed and credited to the provider account as part of step 534.

While not seen in the illustrated EOB statement of FIG. 7, the EOB statement could include an easily read summary (on the statement or in a separate appendix printed at the same time) with "plain English" or simplified explanations for the patient who might otherwise be confused by the detail in the EOB. As an example, the summary might include three lines that simplify the transaction, such as:

"The charge today is $157.74"

"Your health plan has paid $0"

"You owe $157.74"

In cases where the both an estimated EOB statement is transmitted, and then a subsequent, actual EOB statement is transmitted, the statement illustrated in FIG. 7 may be modified to indicate whether or not the statement is estimated. For example, the top of the statement may include the legend "ESTIMATE", with a comment that the patient will subsequently receive an actual EOB statement where amounts may be slightly different than those shown. In addition, a comment may appear for the patient to understand that when the actual EOB statement is received, the patient may have his account (MSA, credit card, banking account) adjusted in order to reconcile any differences between the estimated EOB and the actual EOB.

While the estimating system used for generating an estimated EOB will be described in greater detail later, it should be understood that to alleviate concerns of the patient, the estimating system may be rules based and designed so that amounts returned on the estimated EOB are conservative (e.g., the estimated patient portion may be calculated so that rarely, if ever, will it be more than the actual patient portion after final adjudication). At the same time, the rules used by the estimator system can be designed to satisfy the provider that most if not all of the patient portion determined as due from the patient after final adjudication will be paid at the time that the patient is at the provider's office, rather than waiting for the final EOB statement to be issued by the insurer and subsequently billed by the provider. Furthermore, in some circumstances, the provider may chose to receive authorization from the patient to post a transaction against the patient's account based on the estimated EOB, but process the transaction when the actual EOB is received. While such an arrangement may delay payment to the provider, it eliminates the cost and delay of preparing and sending a separate bill to the patient after receiving the EOB (and waiting for the patient to make payment on that separate bill).

Figure 8:
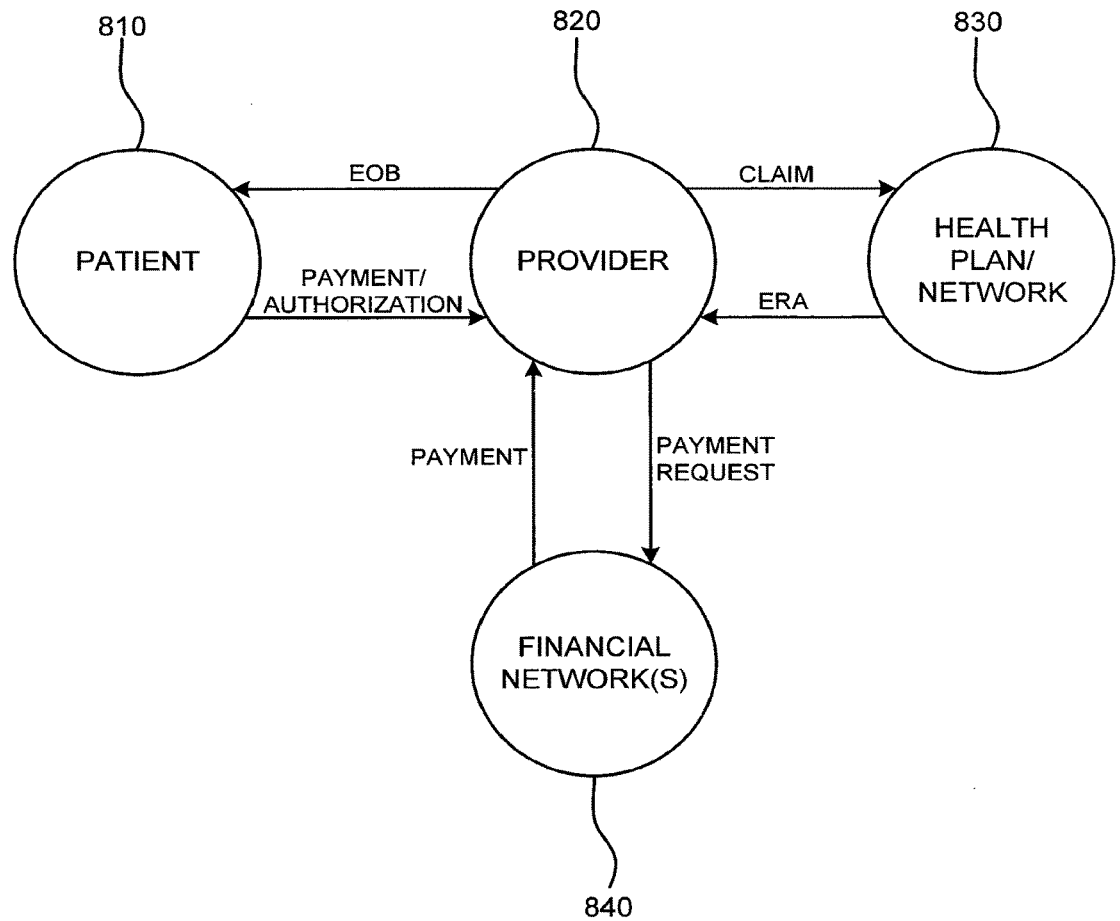
FIG. 8 illustrates the flow of information and payment in accordance with one embodiment of the invention.

FIG. 8 illustrates one embodiment of the invention, particularly the flow of information and payment between the parties involved in the claim adjudication process (patient 810, provider 820, health plan/network 830, and financial network 840). As seen, the provider submits a claim to the health plan and receives back EOB information in the form of an ERA (electronic remittance advice). The EOB is generated and provided to the patient, and the patient makes or authorizes payment for any patient responsibility amount. If a payment for the patient responsibility amount is authorized by the patient through the provider, that authorization or request is sent to the financial networks and payment is credited back to the provider (from an MSA, credit card account, electronic funds transfer, etc.). It should be noted that the embodiment of FIG. 8 contemplates that the provider host 106 (FIG. 1) runs applications having the features and functionality required to manage the flow of information (including claims and payments) between the provider terminals 102, financial network 110 and health networks 116.

Figure 9:
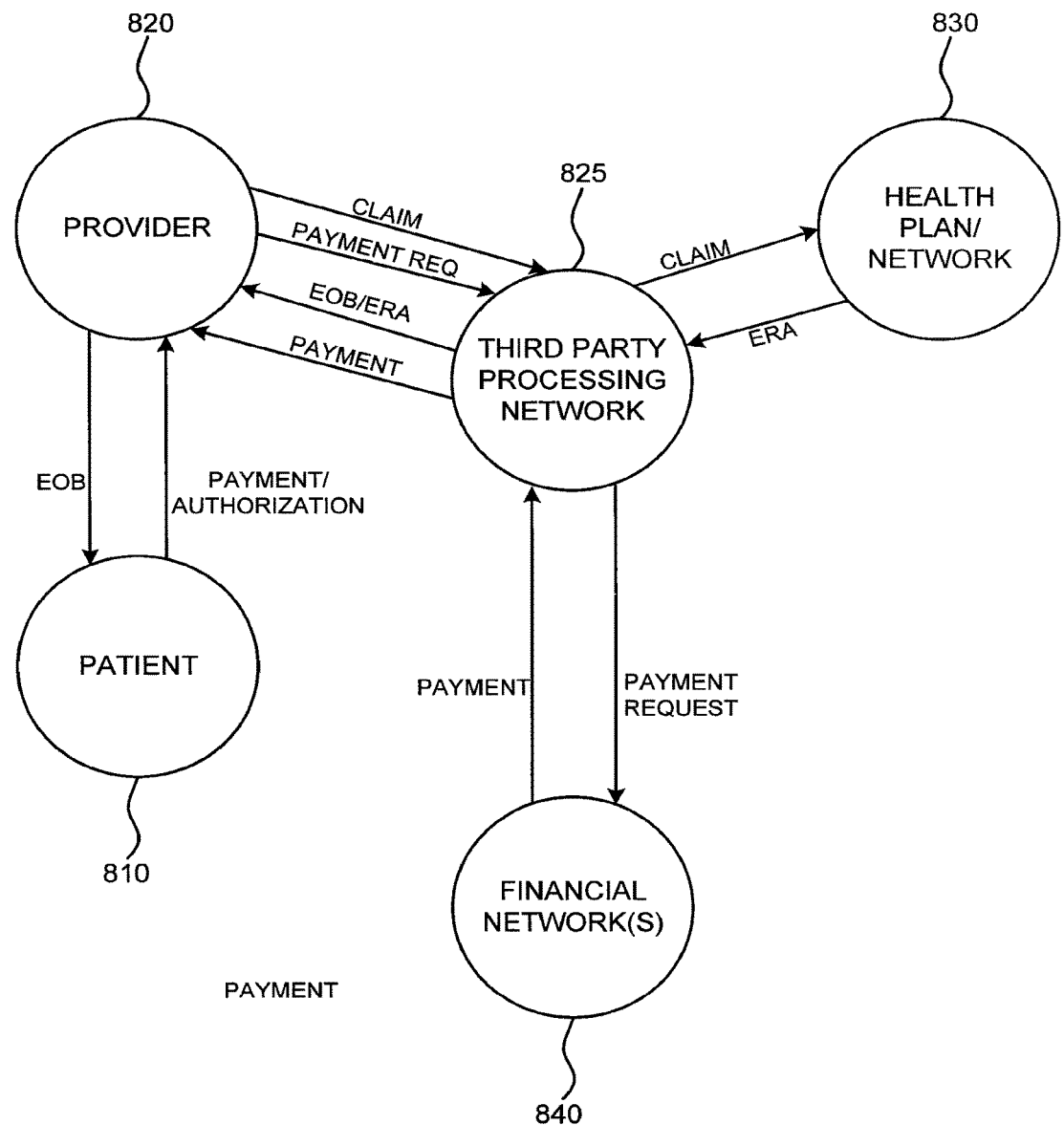
FIG. 9 illustrates the flow of information and payment in accordance with another embodiment of the invention.

FIG. 9 illustrates another embodiment of the invention where in addition to the parties illustrated in the embodiment of FIG. 8, a third party processing entity/intermediary/network 825 is used for processing claims and payments. Such a third party could operate a web host/server that runs applications using POS terminals 102 for generating claims from the provider, submitting those claims to the health plan, receiving back the ERA message and forwarding the ERA message to the provider in order to generate the EOB statement for the patient at the provider POS terminal. In addition, any payment authorization made by the patient is passed through the provider to the third party network where it is routed to the appropriate financial network (as an MSA, credit card, or other payment request/authorization) so that payment may be made back to the provider. One advantage of the third party processing network 825 is that the applications running at the third party network are more sophisticated and could off-load processing and data management from the provider host/terminal (e.g., creating and transmitting claims, EOB data, financial transactions, etc.) which may be beyond the normal capabilities of the systems and staff at the provider location.

In addition, the specialized knowledge and capability of the third party network 825 can considerably reduce the complexity and cost of submitting claims (e.g., by the provider). Among other things, the third party network could evaluate claims information entered by the provider at terminals 102 (on a real-time basis) and request corrections of errors or mis-entered data that would otherwise delay claim processing by the health plan or network 830. For example, if errors or inconsistencies are detected in procedure or diagnosis codes or provider IDs, the network 825 could be programmed to alert the provider (and require correction) while the patient is still present. This is particularly useful when a provider is routinely entering data for claims that go to different health networks, where each may have different requirements for the types of data needed. In each case, the third party network will not pass a claim on to a health network until the claim has been properly completed by the provider.

Figure 10:
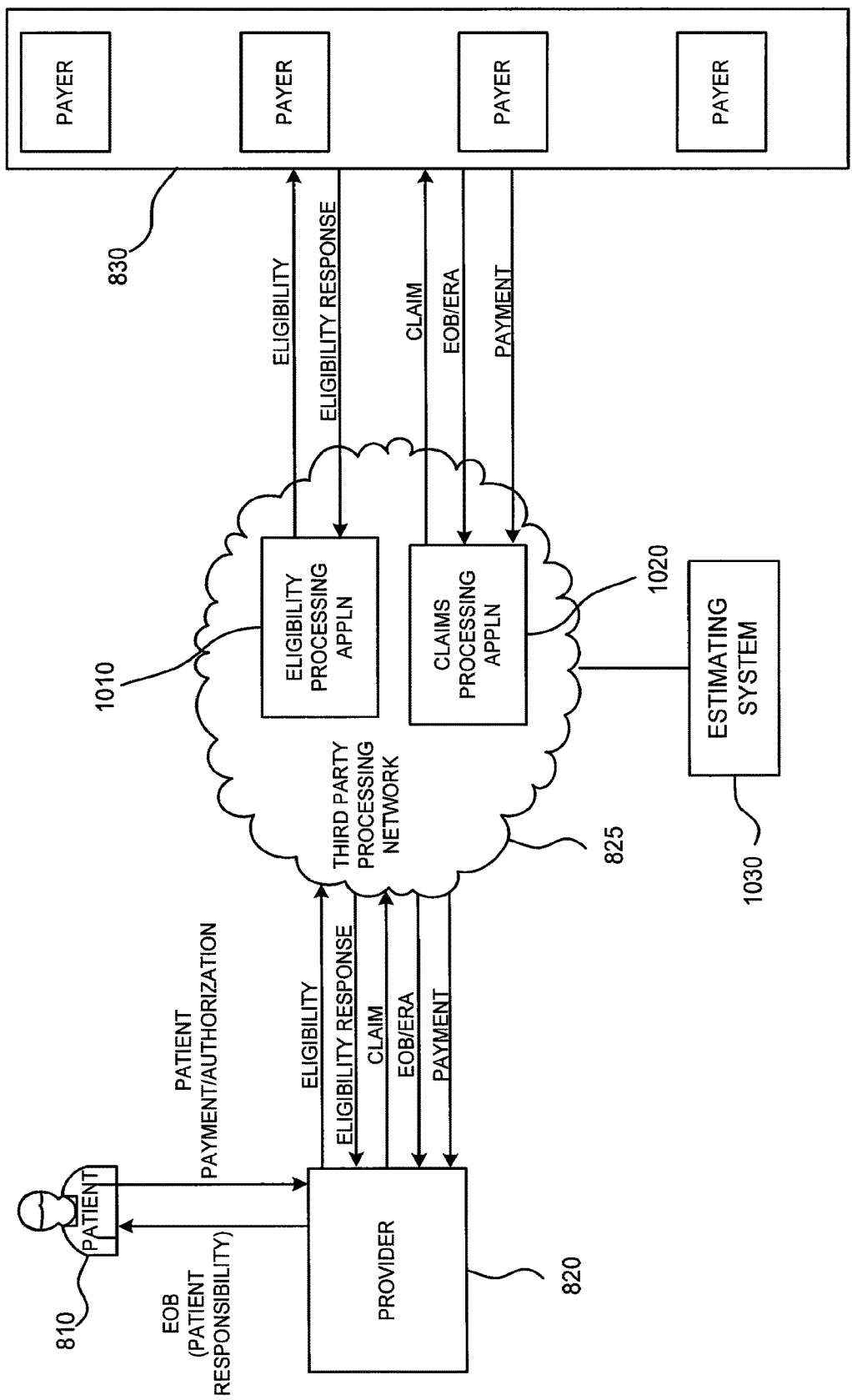
FIG. 10 is a block diagram illustrating a graphical representation of the parties and networks in the embodiment of FIG. 9, including an estimating system for providing estimated EOB information.

Furthermore, the third party network 825 could manage transactions used to pay the patient responsibility portion or amount (e.g., debiting an MSA, credit card, debit card, checking/bank account, etc.). FIG. 10 is a further, graphical representation of the embodiment of FIG. 9, illustrating the patient 810, provider 820, third party network 825 and health plan networks or payers 830. There is associated with the third party network 825 an application or system 1010 for processing eligibility inquires from the provider (i.e., confirmation that the patient 810 is currently enrolled or covered under the identified health plan) as well as an application or system 1020 for processing claims and payments to/from the payers 830 (as described earlier).

While FIGS. 9 and 10 illustrate a single third party processing network 825, there may be optionally two different entities/networks involved. For example, one network could handle or facilitate financial transactions (payments between provider, patient and healthcare network) and the other handle or facilitate elegibility, claims and EOB processing (either directly with the provider or through a financial network).

As also seen in FIG. 10, an estimating system 1030 is used in circumstances where the third party payer of the patient does not have real-time claim adjudication capabilities. By way of explanation, many large insurers have complex claim adjudication systems (often the result of acquiring legacy systems from predecessor companies), and as a result will usually rely on batch processing of claims (including electronic claims) in order to provide EOB data (for example, a day, a week or even longer, after the claim is submitted by the provider/patient). The estimating system 1030 has a rules-based engine for estimating permitted charges and patient portion amounts based on experiences with various health plans and their agreements with providers. Permitted charges are frequently based on the location of the provider (permitted charges are higher is some areas than others, based on economic factors such as cost of living, provider competition, and the like). Furthermore, some third party payers are more aggressive in negotiating permitted charges, and so the identity of the health plan will also influence the estimate. Also, individual payers or insurers may offer multiple plans, and identifying the patient's specific plan within a health insurer system will likewise influence the estimate. Further, the estimating system 1030 may be designed to refine its estimates based on certain experience, i.e., comparing estimated EOB data with actual EOB data for the same claim, and adjusting future estimates (up or down) based on those comparisons. In addition, estimating systems may be designed to weigh other factors, such as the previously mentioned bias toward being conservative (to avoid overestimating the patient portion).

Figure 11:
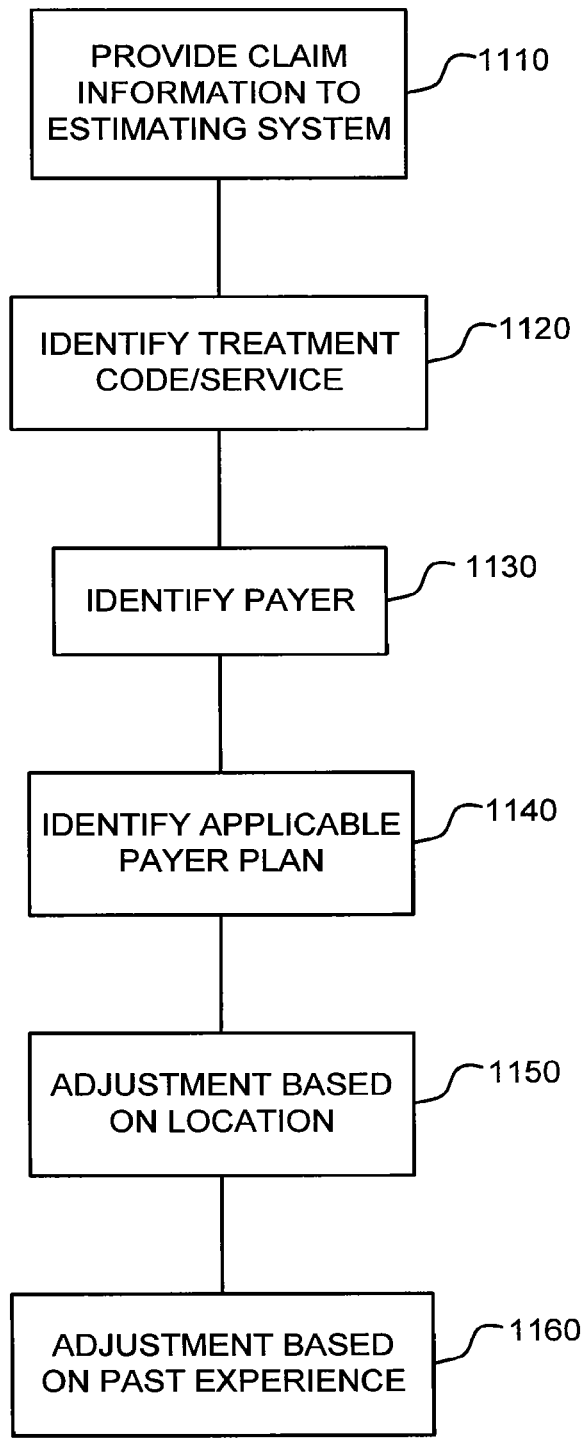
FIG. 11 is a flow diagram illustrating a rules-based decision process that could be used in the estimating system of FIG. 10.

An exemplary process is seen in FIG. 11, illustrating how the rules-based engine in the estimating system might be implemented. As seen, at step 1110 the claim information (collected and submitted by the provider 820 to the network 825) is provided to the estimating system 1030. It should be understood that the network 825 may direct a claim to the estimating system based on a decision based process within network 825 as to whether or not the identified payer is capable of providing real-time EOB information. The estimating system identifies (step 1120) the treatment code of the service for which a charge is being submitted, identifies (step 1130) the payer (insurer), e.g., to determine that payer's usual discount for the service, identifies (step 1140) the specific payer plan under which the patient is covered, and makes adjustments for the location of the provider (step 1150). Finally, the estimating system adjusts estimated amounts (step 1160) based on experiences for similar past claims, i.e., comparisons of prior estimates and their subsequent actual amounts after final adjudication, and making adjustments if the prior estimates have proven to be too high or too low. It should be understood that the order of steps in FIG. 11 may vary, and in some circumstances, further steps/decisions/adjustments may be involved.

Figure 12:
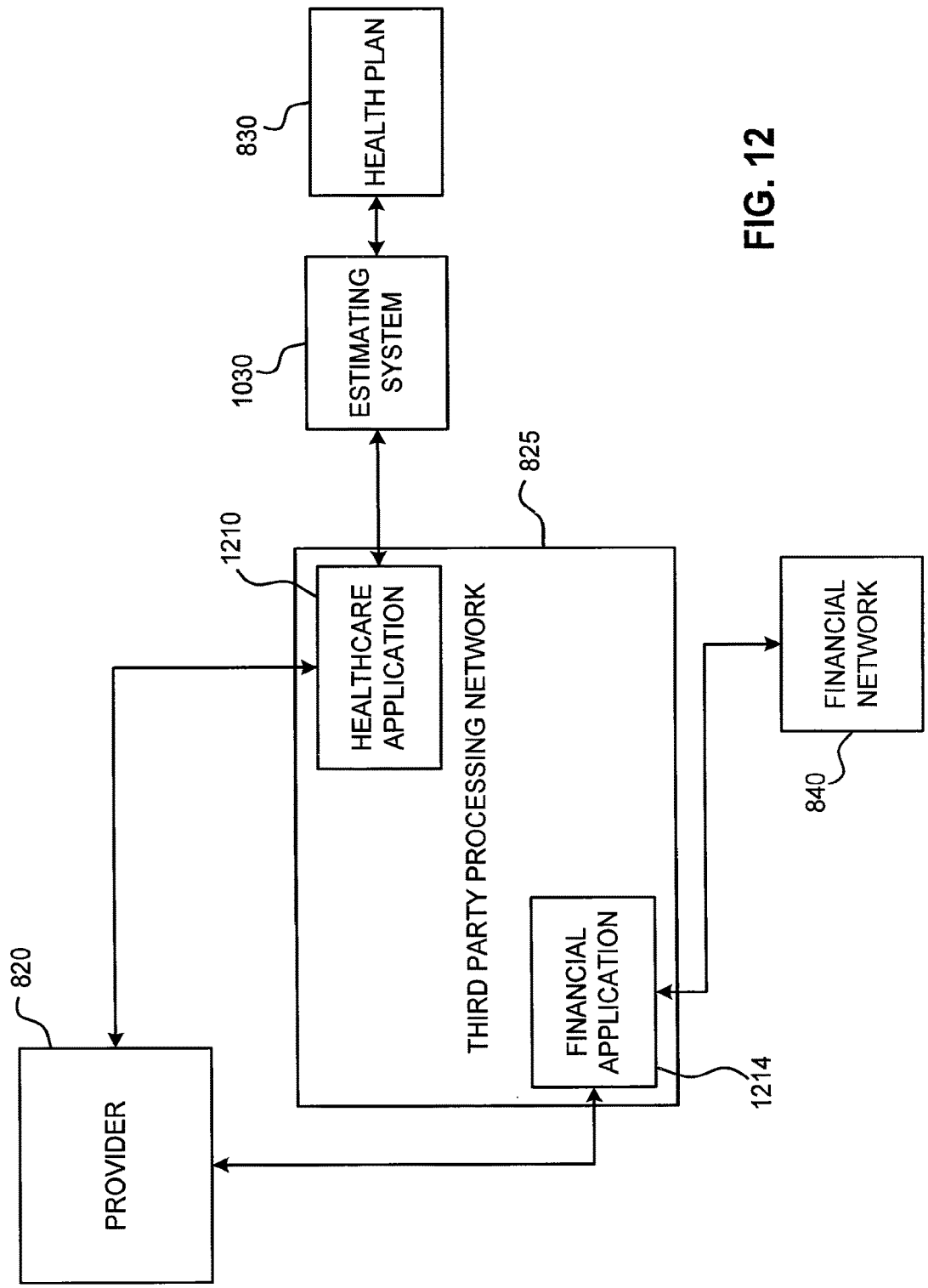
FIG. 12 is a block diagram illustrating another embodiment of the invention, where the estimating system is resident at the first payer.

FIG. 12 illustrates another embodiment of the invention, where the estimating system 1030 is resident at the payer or health plan 830. The estimating system 1030 in FIG. 12 could have the same functionality as discussed earlier in conjunction with FIGS. 10 and 11. However, being located within the health network of the payer provides additional features, such as access to information maintained in the database of the payer. For example, the estimating system could provide more accurate estimates by virtue of having access to deductible information maintained in the database of the payer (e.g., by being able to determine when a deductible had been met, and thereafter basing the estimate on that fact). As in other embodiments, FIG. 12 also has the third party network/host 825 for receiving healthcare claim information from a provider 820. The network 825 includes a healthcare application for creating and processing those claims, and a financial application for handling payment transactions to be posted to MSA, credit card, debit card, or other financial/banking accounts accessed through the financial network 840.

Figure 13:
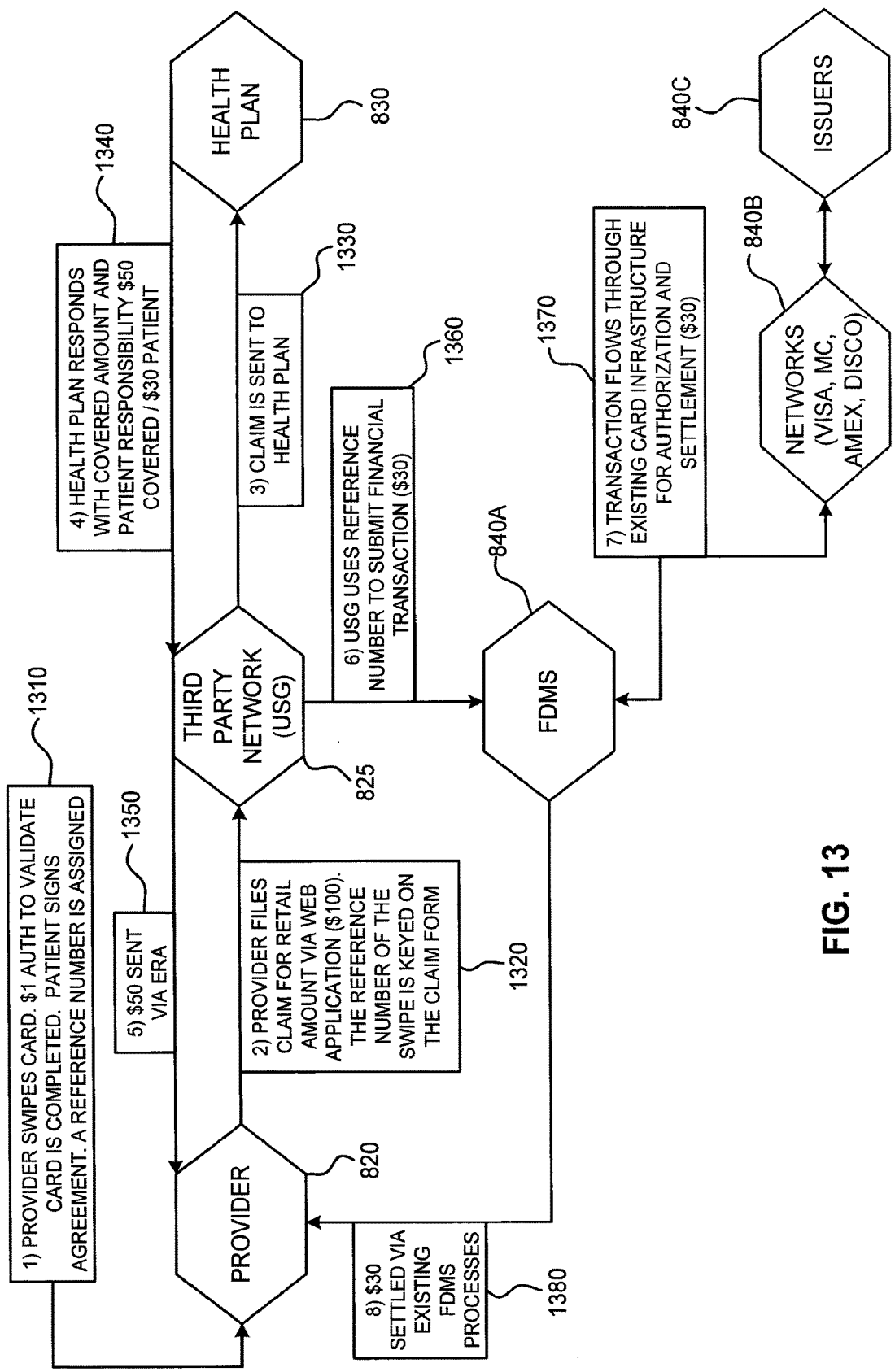
FIG. 13 is a flow diagram illustrating another embodiment of the invention, where a reference number is assigned to each healthcare transaction.

FIG. 13 is a flow diagram of another embodiment of the invention, illustrating the use of a control or reference number that is generated and assigned to an individual healthcare transaction, in order to facilitate payment of the patient responsibility amount. To better understand the process of FIG. 13, the provider (retail) charge for treatment or services provided to the patient is assumed to be $100.

At step 1310 in FIG. 13, the patient provides a card, e.g., either a financial card (MSA card, credit card, debit card, etc.) or health plan card 150 illustrated in FIGS. 2A and 2B (card 150 may store the account number for an MSA, credit card or other financial account). The provider 820 swipes the card to read the account number, and a reference number is assigned (e.g., by the third party network 825) for the transaction, with the patient agreeing to pay any amounts not covered by the health plan 830, and with a nominal authorization ($1) sent through the third party network 825 to the financial network 840. The financial network 840 is illustrated as including a card transaction processing network 840A used by the provider (such as FDMS—First Data Merchant Services), a card network 840B (such Visa®, MasterCard®, American Express®, Discover®, etc.), and a card issuer or bank 840C where the authorization amount is approved. The approval of the authorization assures the provider that the card is valid and that the patient has an account which may be used for the patient responsibility amount. Even though approved, the authorization amount is not charged to the account since at this point the provider does not know the actual amount to be paid by the patient. The reference number is associated with the card or account information that will ultimately be used to pay any amount owed by the patient, and the reference number and account information is stored at a host or server (not shown) in the third party network 825 and assigned to the transaction to be used for paying the provider.

At step 1320, while the patient is still present at the provider office or location, the provider files a claim for the provider's charge using the third party network 825. The reference number assigned at step 1310 is entered as part of the claim (either manually or by having the reference number saved at the provider terminal when the patient card is swiped at step 1310), and is thereafter stored at the third party network 825 and associated with the claim. While not illustrated in FIG. 13, in some cases the card swipe may also identify the patient in order to assist the provider in preparing the claim. The claim is sent to the health plan (step 1330), and on a real-time basis the health plan responds with EOB information (step 1340), including covered amount and patient responsibility (in this case, $80 of the original $100 charge is the allowed amount, with $50 covered by the health plan and $30 to be paid by the patient). It should be appreciated that depending on whether the health plan is able to perform real-time adjudication of a claim, the EOB information from the health plan (or third party network 825) may be either estimated EOB information (from an estimating system resident at the health plan or third party network) or actual EOB information (from real-time adjudication of the claim at the health plan system).

At step 1350, the provider is notified that $50 is being paid to the provider as part of the EOB or electronic remittance advice (ERA). As discussed earlier, the EOB information is sent to the provider so that a statement can be generated at the provider terminal (and displayed or printed for the patient, if desired).

When the EOB data is received by the third party network 825, it uses the reference number previously provided at step 1320 (and the card or account information associated with it) to create and submit a charge or transaction (step 1360) to be processed through the financial network 840 and debited against the patient account for the $30 patient portion of the covered charge (step 1370). When debited against the patient's account, the transaction is then also posted as a credit to an account of the provider in the same manner as the settlement of a conventional credit or debit card transaction (step 1380).

Figure 15:
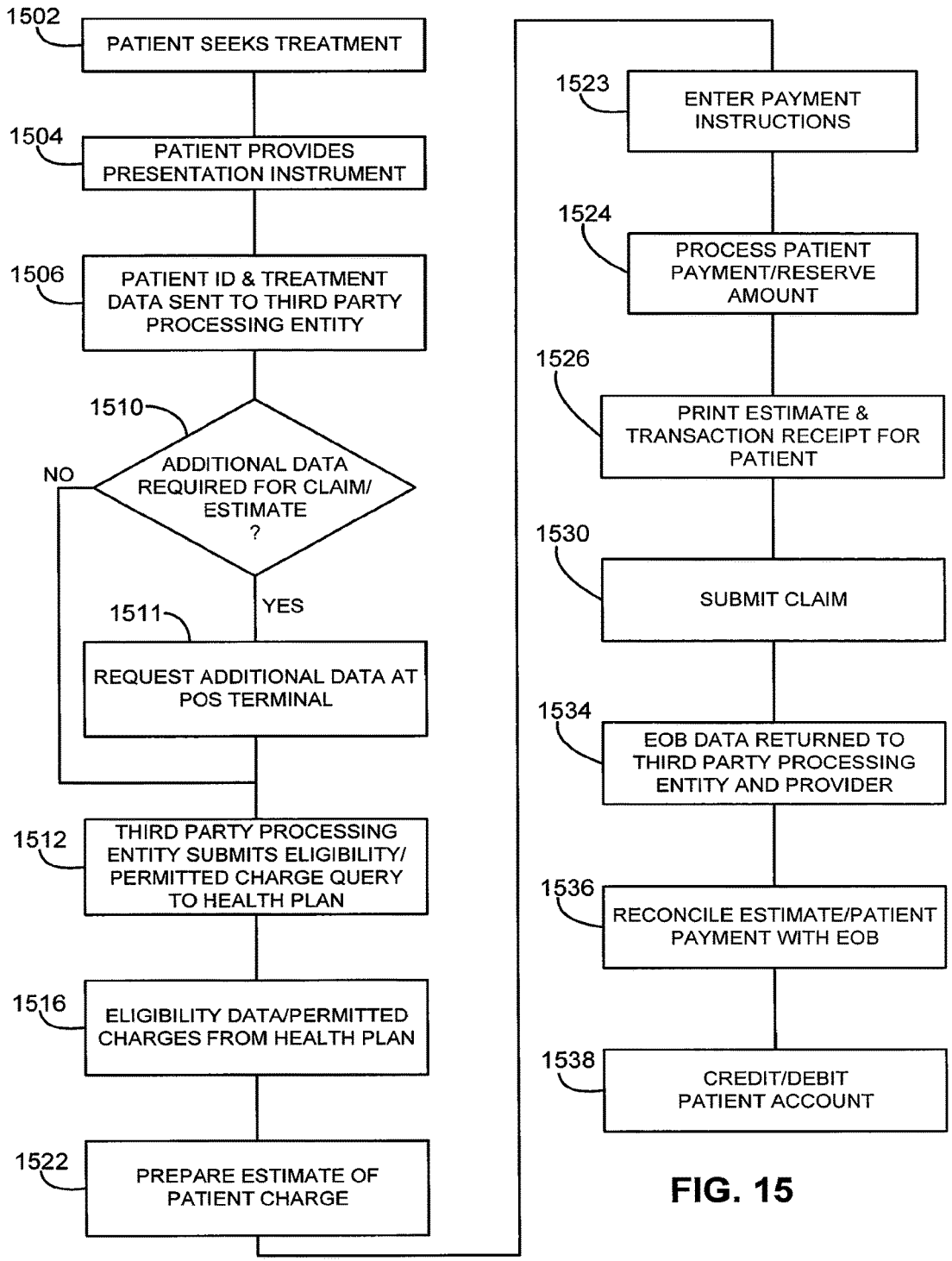
FIG. 15 is a flow diagram illustrating, among other things, a process for providing and using estimated EOB information.

Another embodiment of the invention is illustrated in FIGS. 14 and 15. In this embodiment, the processing of estimates, submission of electronic claims (on behalf of the provider and patient), and the processing of payments from the patient are all handled through the third party processing entity/network 825. The third party processing entity will estimate a patient portion based on the available information that may be returned by a health plan in response to one or more preliminary requests for information from the third party processing entity (and in accordance with parameters established or agreed to by the provider).

As explained earlier, many insurers and health plans are not able to provide on-line, real-time processing of claims due to the complexity of their systems, and such claims are batch processed—often at the end of each business day. In the case of a provider that submits information electronically (either directly or through a third party processing entity), the claim will often be processed at the end of the business day that the claim was received, and so even though in some circumstances (depending on the frequency of processing) the EOB might be generated (and could be sent to the provider) within 12 hours of the electronic claim submission, it will be received after the patient has left the office of the provider. Even without using a sophisticated rules-based estimating system, a third party processor may be able to obtain sufficient information from the health network in order to estimate a patient portion that can later be reconciled with an EOB, so that the estimated patient portion may be paid (or authorized) when the patient is still at the provider's office.

In particular, two levels of information may be accessible to the third party processing entity (from the health plan) even though the claim cannot be processed by the health plan on a real-time basis. One level is eligibility information, which will tell the provider whether the patient in question is covered under the health plan, and also the general terms of the plan coverage (e.g., deductible amount, co-pays, non-covered procedures/services, etc.). A second and more detailed level of information will include the allowed or permitted amount that may be charged for the particular service or treatment. This is not always available on a real-time basis (and hence is not part of the first level of information), because for many health plans the permitted charges for services may be a complex set of data, with each permitted charge depending not only on the particular service provided, but also the particular provider providing the service.

Information not typically available at either of the two levels (until after claims are batch processed) would be the previous charges and previous payments applied to deductibles. The deductible remaining at any given time may change day-to-day, depending on whether a claim has been submitted on that day.

Even though an estimate pursuant to the embodiment illustrated in FIGS. 14 and 15 may not be precise (since it may be based on varying levels of health plan information), it does provide significant advantages to the provider in minimizing losses due to late payment or non-payment by patients. For example, after a patient has received services, the provider can determine (though the third party processor) whether the patient is insured, and what level of deductible is applicable. If the person has a high deductible, the provider can assume that the patient may be responsible for most if not all of the charge. Further, if co-pays are applicable to a specific service, then regardless of whether the patient has met the deductible, he/she will be responsible for at least that portion of the charge. If the second level of information is available, (i.e., the permitted charge for the service), the provider will know the maximum that the patient will be responsible for (regardless of deductibles), since the permitted charge is the maximum that can be charged pursuant to the agreement between the provider and the health plan. As examples only, and depending on the level of financial risk that the provider is willing to assume, the provider may collect (or alternatively, obtain authorization approval—i.e., reserve an amount against the patient's credit limit on a credit card using an approved authorization request) one of several different amounts as an estimated charge, such as (1) the full, undiscounted amount of the fee or charge (e.g., if the permitted charge is not known), or (2) the full amount of the permitted charge (if known), or (3) the co-pay amount for the service. The advantage of posting an authorization for a transaction against the patient's credit card account at the time of service is that the amount is reserved against the patient's credit limit (and available for later use in satisfying the charge). The posting of the actual charge itself can be delayed until the EOB is received (typically the following day). Obtaining prior authorization for a transaction assures the provider that once the estimated amount is reconciled with the EOB, the provider will be able to process the charge without having it rejected because of credit limit restrictions on the patient's credit card account.

Although three examples are provided above for amounts to be posted (or for which authorization is obtained) against the patient's credit card account, other amounts could be used by the provider (and authorized by the patient while at the providers office), depending on the financial risk the provider is willing to assume and, of course, the provider's relationship with the patient.

If the provider desires, he/she may post the estimated charge against the patient's credit card account as a purchase transaction (rather than as a reserve/authorization), and then post a credit later for any overcharge that results from reconciliation with the EOB.

Referring now to FIG. 14, there is illustrated an estimated EOB that is displayed on the provider POS terminal 102, using health plan information relating to a patient in response to an eligibility/claim submission made through the third party processing entity 825. As mentioned above, in some cases the health plan will return basic eligibility information and basic plan features or terms, and in other cases (depending on the accessibility of the health plan databases (DBMS 120 and database 122—FIG. 1), it may also return permitted provider charges). Also, the third party processing entity 825 may submit an eligibility request at the same time or about the same time as a claim submission. In other cases, the eligibility request and claim submission may be one in the same, in which case the health network returns eligibility information/permitted charges as a real-time response to the claim, with the claim then placed into the health network queue for batch processing later. The final EOB could be sent electronically to the provider at the end of the same day as the eligibility request/claim submission, or at the beginning of the following day (in some cases, depending on the health plan, it may take longer).

In FIG. 14, the estimate has a format similar to the EOB illustrated in FIG. 7. The data message sent to the provider could be similar to the data packet illustrated in FIG. 6 (formatted in accordance with ANSI 835). The estimate includes information relating to the service (Service Codes 1402 and Service Descriptions 1404), and for each service or treatment, the Service Date(s) 1406, the Provider Charge 1408, the Allowed Amount 1410 (which is the Provider Charge 1408 less a Discount Amount 1412) and an Amount Not Covered 1413 (e.g., certain services or treatment may be excluded under the patient's plan). Also, certain services may involve a Co-Pay 1418.

In addition, the estimate includes a Patient Plan Summary 1419 that explains certain features of the patient's plan (e.g., the amount of the annual deductible, co-pays, and services excluded or not covered under the plan), an estimated Patient Portion 1420 and a Payment Menu 1432.

In the particular example illustrated in FIG. 14, the Patient Portion 1420 is estimated at $225.00. The provider has chosen to consider the full undiscounted provider charge as the estimate. It should be appreciated that the provider could be more conservative in the estimate, and instruct the third party processor to only estimate the charge based on the charges that are not covered or that have co-pays. Such handling of the estimate will depend on the parameters established by either the provider or the third party processor. In most cases, the provider may want to limit the need for subsequently charging the patient for any underestimated charges, and thus without deductible information, the provider will typically want to have authorization from the patient to charge either the Allowed Amount 1410 (if available) or the full, undiscounted Provider Charge 1408 (if the Allowed Amount is not available), with a reconciliation being done when the actual, final EOB is received. While FIG. 14 illustrates the authorization and the reconciliation being made against a patient's credit card account, it could also be made against an MSA account, a bank account, or other account of the patient.

FIG. 15 illustrates a process for estimating a patient portion of a provider charge, electronically submitting a claim, and later reconciling the claim against the earlier estimate.

As illustrated, the patient first seeks treatment from a provider at step 1502, and then provides a presentation instrument when the patient's charge is to be processed (step 1504). The card 150 (FIGS. 2A and 2B) is read at the POS terminal 102 so that the patient's identifying data (along with any treatment data) may be sent to the third party processing entity 825 at step 1506. The third party processing entity determines whether any additional information is required to complete the estimate at steps 1510 and 1511. It should be noted that the information required at this point at the POS terminal will be similar to the information needed to submit a claim to a health plan. In some cases the request for an estimate may be submitted prior to the submission of a claim, although in other cases, an electronic claim will be automatically treated as a request for eligibility or permitted charge information from the health plan if the health plan cannot handle an electronic claim on a real time basis (in such case, the estimate information is returned to the provider through the third party processing entity, and the claim is put in a queue for later batch processing).

After all required information is collected, the third party processing entity assembles the data and submits it to the health plan (step 1512). Eligibility information (and permitted charges, if available) is returned from the health plan to the third party processor (step 1516). While the third party processing entity may not have a complex rules-based processing engine for estimating the charge (depending on the desired accuracy of the estimate), it can take into account preferences of the provider in calculating the estimate. For example, if the patient had a low deductible health plan (say $100), the third party processing entity may assume that the deductible has been met when calculating the estimate). The third party processing entity may also take into account co-payments and exclusions (services not covered) in the calculation. The third party processing entity prepares the estimate for transmission to the provider (step 1522), where it is displayed at the POS terminal 102 for the patient to authorize payment using an MSA, credit card or other account. Payment instructions from the patient are entered at the POS terminal 102 (step 1523). The payment is processed by the third party processing entity at step 1524, and a printed receipt is prepared by the provider for the patient (the printed receipt may be a print out of the estimate illustrated in FIG. 14).

The third party processing entity uses the data entered at the POS terminal 102 to prepare and submit an electronic claim to the health plan at step 1530 (if it has not been submitted as part of the request for an estimate). After the electronic claim has been batch processed by the health plan, and an electronic EOB data packet (similar to that described earlier in conjunction with FIGS. 6 and 7) is returned to the third party processing entity and the provider at step 1534 (a copy may also be mailed to the patient, inasmuch as the EOB will be generated after the patient has left the provider's office). The third party processing entity reconciles the final or non-estimated EOB with the earlier estimate, step 1536. As a result of the reconciliation, a credit or debit may be made against the patients account (step 1538). For example, if the provider had obtained an authorization against the patient's credit card account for the estimated charge, and such estimate is larger than the actual patient portion in the EOB, then the difference is subtracted from earlier authorized amount and the actual patient portion is then posted against the patient account. Alternatively, if the provider had posted an actual transaction in the amount of the earlier estimate against the account as a purchase, then a credit for the difference is posted against the account on behalf of the provider.

While a detailed description of presently preferred embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A system for providing right-time claim adjudication and payment for patient healthcare services that are provided at a provider location, where payment may be made by multiple payer sources, the system comprising:

a point of sale (POS) device for use by a provider in entering patient information for a patient, including at least patient ID information associated with the patient and a healthcare treatment code for the patient healthcare services provided to the patient;

a display device communicatively coupled to the POS device;

a host computer for receiving the patient information from the POS device, for submitting the patient information as a healthcare claim to a first payer source after the patient healthcare services have been provided to the patient, for submitting the patient information to an estimating system, for receiving from the estimating system estimated explanation of benefits (EOB) information in the form of an estimated EOB statement and in response to the healthcare claim, and for providing the estimated EOB information to the EOS device for display at the display device, the estimated EOB information generated by the estimating system as an estimated adjudication of the healthcare claim and including at least information on an estimated patient portion amount of a provider charge that is not to be paid by the first payer source;

whereby the patient authorizes payment of the patient portion on a real-time basis to the provider while the patient is at the provider location in response to the estimated EOB information displayed at the display device associated with POS device; and wherein the first payer source provides to the host computer final EOB information in the form of a final EOB statement in response to the healthcare claim to the first payer source and based on adjudication of the healthcare claim, the final EOB information separate from the estimated EOB information, and wherein a patient portion amount in the separate final EOB information is reconciled against the patient portion amount, in the estimated EOB information.

2. The system of claim 1, wherein the estimated EOB information further includes information relating to a permitted charge corresponding to the treatment code.

3. The system of claim 1, wherein the patient authorizes payment of the patient portion from a second payer source.

4. The system of claim 3, wherein the second payer source is selected from a group consisting of a credit card account, debit card account, MSA, or a bank account.

5. The system of claim 4, wherein the host computer receives information on the second payer source and electronically posts the amount of the patient portion as a transaction against the second payer source.

6. The system of claim 4, wherein the host computer receives information on the second payer source, and wherein the second payer source is a credit card account and wherein authorization of payment is a reserve against a credit limit for the account.

7. The system of claim 5, wherein the estimated EOB information further includes information on a permitted charge corresponding to the patient information.

8. The system or claim 1, wherein the host computer is operated by a third party transaction processing entity, wherein the third party transaction processing entity is a party other than the provider and the first payer source.

9. The system of claim 1, wherein the host computer is operated by the provider.

10. The system of claim 1, wherein the display device associated with the POS device displays information on at least one of the payer sources other than the first payer source, so that the other payer source may be selected for the patient portion, thereby permitting real-time payment of the patient portion by the selected payment source, while the patient is at the provider location.

11. The system of claim 10, wherein the first payer source is a healthcare insurer, and wherein the selected other payer source is an MSA account.

12. The system of claim 10, wherein the first payer source is a healthcare insurer, and wherein the selected other payer source is a financial account maintained by the patient.

13. The system of claim 12, wherein the financial account maintained by the patient is a credit card account.

14. The system of claim 12, wherein the financial account maintained by the patient is a banking account.

15. The system of claim 1, wherein the host computer determines whether the first payer is able to provide real-time adjudication of the healthcare claim, and submits the healthcare claim to the estimating system when the first payer is not able to provide real-time adjudication of the healthcare claim.

16. A method for making payment on a charge from a provider for healthcare services that are provided to a patient at a provider location, wherein the services are subject to a healthcare plan administered by a first payer, and wherein a patient portion amount of the charge may not be covered by the healthcare plan, and wherein a second payer may be used for the patient portion, the method comprising:

providing a healthcare provider system at the provider location, the provider system having a point of sale (POS) device for receiving a patient ID and a treatment code identifying healthcare services provided to the patient, and the provider system for identifying the first payer;

electronically preparing a claim at the provider system for the first payer, the claim including the patient ID ) and the treatment code, after the patient healthcare services have been provided;

transmitting the claim from the provider system to the first payer and to an estimating system;

generating estimated EOB data at the estimating system as an estimated adjudication of the claim and in response to the claim, and transmitting the estimated EOB data to the provider system, the estimated EOB data representing at least the patient portion amount;

displaying the estimated EOB data at a display device associated with the POS device at the provider system for the patient to authorize payment from the second payer for the patient portion amount based on the estimated EOB data;

electronically submitting an authorization for payment from the provider system to a second payer system, in order to process real-time payment from the second payer while the patient is at the provider location;

subsequently receiving at the provider system non-estimated EOB data from the first payer in response to the claim and that is separate from the estimated EOB data; and reconciling the non-estimated EOB data against the estimated EOB data.

17. The method of claim 16, wherein the patient ID is received at the provider system by reading a presentation instrument.

18. The method of claim 16, wherein a processing system operated by a third party processing entity generates the estimated EOB data, submits the claim to the first payer system, processes authorization for payment to the second payer system, and reconciles the non-estimated EOB data against the estimated EOB data, and wherein the third party processing entity is a party other than the provider, the first payer and the second payer.

19. The method of claim 16, wherein the healthcare plan is a high deductible plan.

20. A system for making payment for patient healthcare services to a provider of such services, where payment may be made by multiple payer sources, including a first payer to whom a health care claim is submitted and a second payer maintaining an account on behalf of the patient that may be used for amounts not paid by the first payer, the system comprising:

a point of sale (POS) device for use by the provider in entering data, including at least a patient identification and a treatment code;

a display device associated with the POS device; and a healthcare network linked to the POS terminal and to the second payer, the healthcare network for:

receiving data entered at the POS terminal and in response to the received data electronically transmitting a healthcare claim to the first payer source and to an estimating system, after patient healthcare services have been provided to the patient;

receiving from the estimating system an estimated explanation of benefits (EOB) message in response to the healthcare claim and after patient healthcare services have been provided to the patient, as an estimated adjudication of the healthcare claim, the estimated EOB message provided to the POS device for display at the display device, the estimated EOB message including at least (a) information on a permitted charge corresponding to the treatment code and (b) information relating to a patient portion of such permitted charge that is not to be paid by the first payer; and posting an electronic transaction against the second payer account in response to receipt of the patient portion information, so that real-time payment of the patient portion to the provider may be made while the patient is at the provider location and after the estimated EOB message is received by the healthcare network and provided to the POS device;

wherein the healthcare network subsequently receives a non-estimated EOB message from the first payer in response to the healthcare claim, and where a patient portion of the non-estimated EOB message is reconciled by the healthcare network against the patient portion of the estimated EOB message; and wherein the difference between the estimated EOB information and the non-estimated EOB information is used by the estimating system as a basis for calculating estimated EOB information for subsequent healthcare claims transmitted to the estimating system.

21. The system of claim 20, wherein:

the POS device receives information relating to the second payer account while the patient is at the provider location;

the healthcare network assigns a reference identifier associated with the second payer account and associates the reference identifier with the healthcare claim; and the healthcare network uses the reference number to identify the second payer account when the estimated EOB is received from the estimating system, in order to post a transaction against the second payer account.

22. The system of claim 21, wherein the healthcare network includes a host computer linked to the POS device and to the second payer.

23. The system of claim 22, wherein the healthcare network includes the estimating system, wherein the healthcare network is operated by a third party processing entity, and wherein the third party processing entity is a party other than the provider, the first payer and the second payer.

* * * * *